(12) United States Patent
White et al.

(10) Patent No.: US 6,939,704 B1
(45) Date of Patent: Sep. 6, 2005

(54) ENHANCED EXPRESSION OF PROTEINS IN GENETICALLY MODIFIED FUNGI

(75) Inventors: Theresa C. White, Ottawa (CA); Sylvia McHugh, Gloucester (CA); Christopher D. Hindle, Gloucester (CA)

(73) Assignee: Iogen Energy Corporation, Ontario (CA)

( * ) Notice: Subject to any disclaimer, the term of this patent is extended or adjusted under 35 U.S.C. 154(b) by 0 days.

(21) Appl. No.: 09/392,476

(22) Filed: Sep. 9, 1999

Related U.S. Application Data

(63) Continuation-in-part of application No. 09/037,524, filed on Mar. 10, 1998, now Pat. No. 6,015,703.

(51) Int. Cl.$^7$ .............................. C12N 9/42; C12N 9/44; C07H 21/04
(52) U.S. Cl. ........................ 435/209; 435/189; 435/210; 435/254.11; 435/254.3; 435/254.4; 435/254.5; 435/254.6; 435/254.7; 435/320.1; 536/23.2
(58) Field of Search .................................. 435/189, 209, 435/210, 254.11, 254.3, 254.4, 254.5, 254.6, 254.7, 320.1, 69.1, 183, 254.1; 536/23.2, 23.1; 530/350

(56) References Cited

U.S. PATENT DOCUMENTS

| | | | | |
|---|---|---|---|---|
| 5,591,619 A | * | 1/1997 | Xin-Liang et al. | 435/201 |
| 6,015,703 A | | 1/2000 | White et al. | 435/209 |

FOREIGN PATENT DOCUMENTS

| | | | |
|---|---|---|---|
| WO | WO 90/15860 | 12/1990 | |
| WO | WO 92/10581 | 6/1992 | |
| WO | WO 93/00426 | 1/1993 | C12N/9/20 |
| WO | WO 93/12237 | 6/1993 | |
| WO | WO 93/24621 A1 * | 12/1993 | C12N/9/24 |
| WO | WO 97/27306 | 7/1997 | |

OTHER PUBLICATIONS

Barnett et al., "Cloning and Amplification of the Gene Encoding an Extracellular β–Glucosidase from *Trichoderma reesi*: Evidence for Improved Rates of Saccharification of Cellulosic Substrates", *Bio/Technology*, vol. 9, p. 562–567, (1991).

Paradis, F.W. et al., "Expression and Secretion of Beta–Glucuronidase and Pertussis Toxin S1 by *Streptomyces lividans*", *Appl. Microbiol. Biotechnol.*, vol. 45, pp. 646–651, (1996).

Van Gemeren, L.A. et al., "The Effect of Pre– and Pro–Sequences and Multicopy Integration on Heterologous Expression of the *Fusarium solani* Pisi Cutinase Gene in *Aspergillus awamori*", *Appl. Microbiol. Biotechnology*, vol. 45, pp. 755–763 (1996).

Ghosh, A. et al., "Cellulass Secretion from A Hyper–Cellulolytic Mutant of *Trichoderma ressei* Rut–C30", *Archives of Microbiology*, vol. 140, No. 2–3, pp. 126–133, (1984).

Keränen, S. and Penttilä, M., "Production of Recombinant Proteins in the Filamentous Fungus *Trichoderma reesei*", *Current Opinion in Biotechnology*, vol. 6, pp. 534–537 (1995.

Torronen et al., "The Two Major Xylanases from *Trichoderma reesei*: Characterization of Both Enzymes and Genes," *Bio/Technology*, 10: 1461–1465, (1992).

* cited by examiner

*Primary Examiner*—Robert A. Wax
(74) *Attorney, Agent, or Firm*—Fitzpatrick, Cella, Harper & Scinto

(57) ABSTRACT

The present invention relates to increasing the production of a protein of interest from a fugal host. The invention discloses nucleotide sequences comprising, a regulatory region in operative association with xylanase secretion sequence and a gene of interest. The gene of interest encodes a protein selected from a pharmaceutical, nutraceutical, industrial, animal feed, food additive and an enzyme. Preferably, the gene of interest encodes a cellulase, hernicellulase, a lignin degrading enzyme, pectinase, protease, or peroxidase. The present invention also relates to vectors and hosts comprising these nucleic acid sequences, and to methods for the production of a protein of interest.

27 Claims, 11 Drawing Sheets

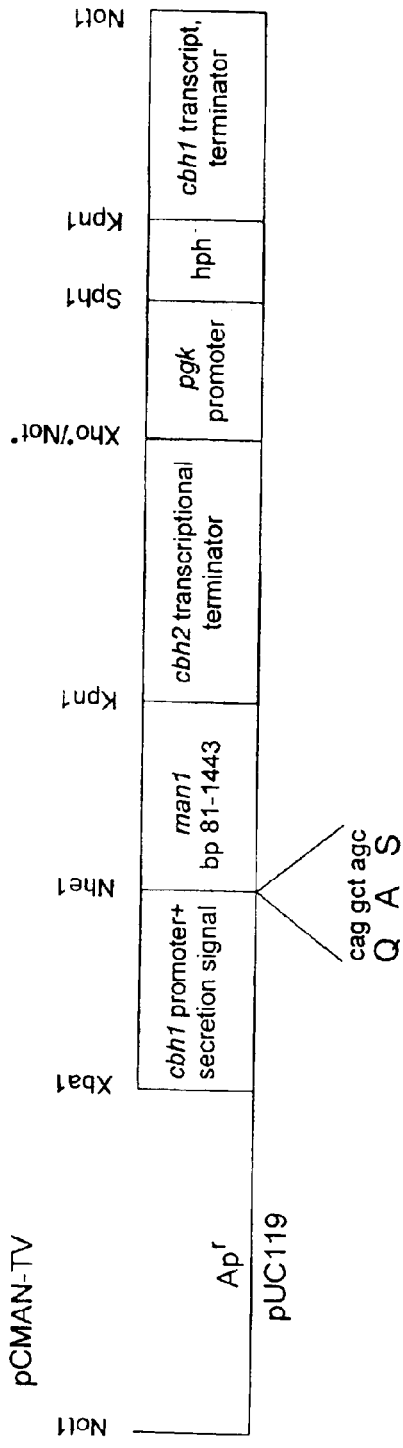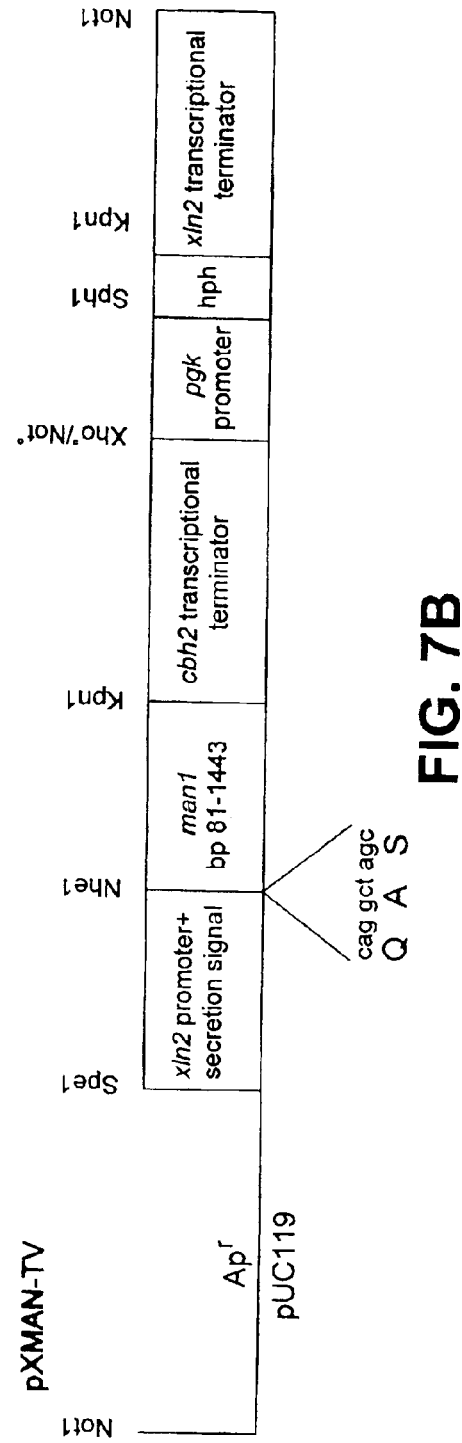

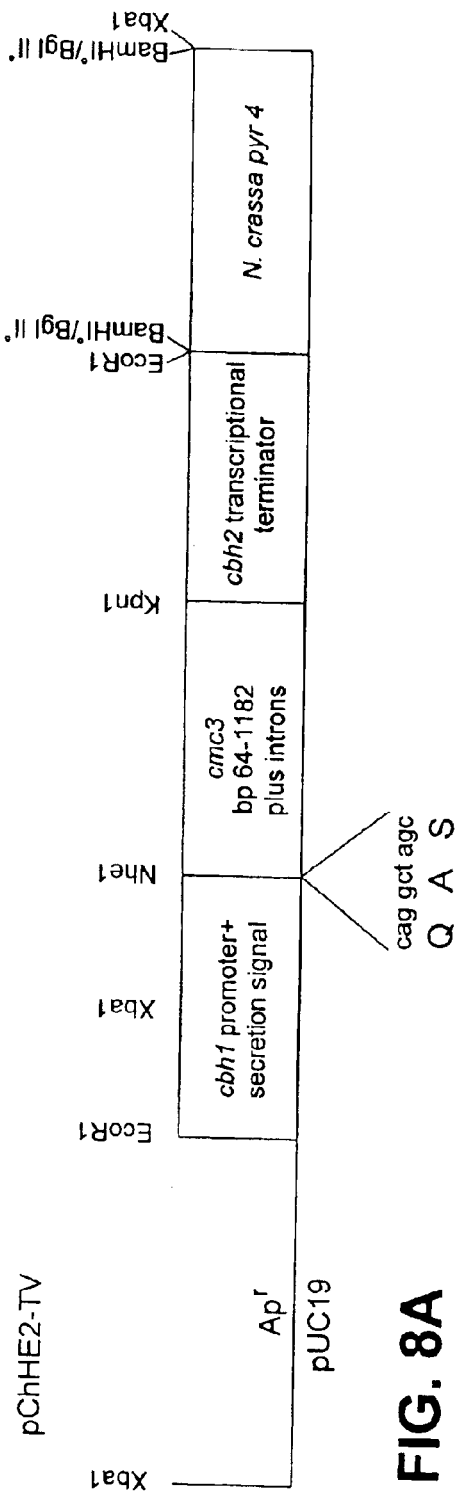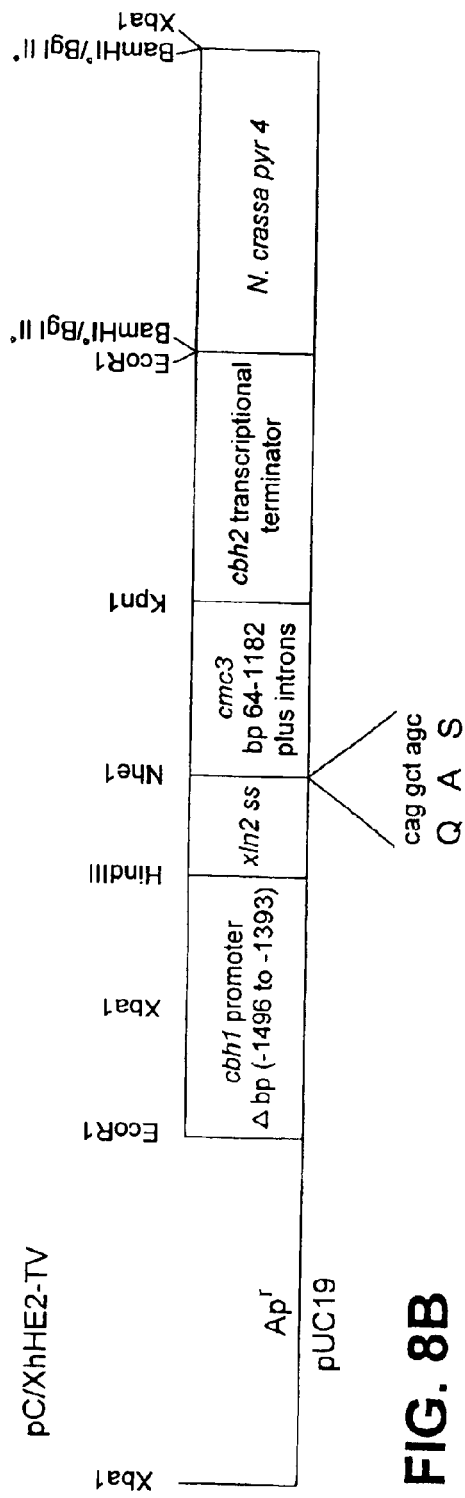

ENHANCED EXPRESSION OF PROTEINS IN GENETICALLY MODIFIED FUNGI

This application is a continuation-in-part of application Ser. No. 09/037,524 filed Mar. 10, 1998 now U.S. Pat. No. 6,015,703.

BACKGROUND OF THE INVENTION

1. Field of the Invention

This invention relates to genetic modification of fungi to enhance production of a protein of interest. Furthermore, this invention relates to novel genetic constructs that dramatically increase the amount of protein produced by fungi containing these constructs.

2. Background of the Related Art

The use of fungal expression systems for the production of proteins of interest is well known within the art. For example, heterologous proteins have been produced within fungal expression systems for biomass conversion, detergent applications, de-pilling of cellulase substrates and other industrial enzyme uses. The production of other heterologous proteins of interest, such as food additives or supplements, pharmaceutical compounds, antibodies, protein reagents and the like, and industrial proteins is also feasible within fungal expression systems.

Many microbes make enzymes that hydrolyze cellulose, including the wood rotting fungus *Trichoderma*, the compost bacteria *Thermomonospora, Bacillus*, and *Cellulomonas; Streptomyces*; and the fungi *Humicola, Aspergillus* and *Fusarium*. The enzymes made by these microbes are mixtures of proteins with three types of actions useful in the conversion of cellulose to glucose: endoglucanases (EG), cellobiohydrolases (CBH), and β-glucosidase. EG and CBH enzymes are collectively referred to as "cellulase". EG enzymes cut the cellulose polymer at random locations, opening it up to attack by CBH enzymes. As an example, *Trichoderma* strains produce at least four distinct EG enzymes, known as EGI, EGII, EGIII, and EGV. CBH enzymes sequentially release molecules of cellobiose from the ends of the cellulose polymer. Cellobiose is the water-soluble β-1,4-linked dimer of glucose. There are two primary CBH enzymes within *Trichoderma*, CBHI and CBHII. β-glucosidase enzymes hydrolyze cellobiose to glucose. *Trichoderma* makes one β-glucosidase enzyme.

This final step in the cellulose hydrolysis which is catalyzed by β-glucosidase is important, because glucose is readily fermented to ethanol by a variety of yeasts while cellobiose is not. Any cellobiose remaining at the end of the hydrolysis represents a loss of yield of ethanol. More importantly, cellobiose is an extremely potent inhibitor of the CBH and EG enzymes. Cellobiose decreases the rate of hydrolysis of the *Trichoderma* CBH and EG enzymes by 50% at a concentration of only 3.3 g/L. The decrease in rate of hydrolysis necessitates the addition of higher levels of cellulase enzymes, which adversely impacts the overall process economics. Therefore, the accumulation of cellobiose during hydrolysis is extremely undesirable for ethanol production.

Cellobiose accumulation has been a major problem in enzymatic hydrolysis because *Trichoderma* and the other cellulase-producing microbes make very little β-glucosidase. Less than 1% of the total protein made by *Trichoderma* is β-glucosidase. The low amount of β-glucosidase results in a shortage of capacity to hydrolyze the cellobiose to glucose and an accumulation of 10 to 20 g/L of cellobiose during hydrolysis. This high level of cellobiose increases the amount of cellulase required by 10-fold over that if an adequate amount of β-glucosidase were present.

Several approaches have been proposed to overcome the shortage of β-glucosidase in cellulase enzymes.

One approach has been to produce β-glucosidase using microbes that produce little cellulose, and add this β-glucosidase exogenously to cellulase enzyme to enhance the hydrolysis. The most successful of such β-glucosidase producing microbes have been *Aspergillus niger* and *Aspergillus phoenicis*. B-glucosidase from these microbes are available commercially as Novozym 188 from Novo Nordisk. However, the quantities required are much too costly for a commercial biomass to ethanol operation.

A second approach to overcoming the shortage of β-glucosidase is to carry out cellulose hydrolysis simultaneously with fermentation of the glucose by yeast, the so-called simultaneous saccharification and fermentation (SSF) process. In an SSF system, the fermentation of the glucose removes it from solution. Glucose is a potent inhibitor of β-glucosidase, so SSF is an attempt to increase the efficiency of β-glucosidase. However, SSF systems are not yet commercially viable because the operating temperature for yeast of 28° C. is too low for the 50° C. conditions required by cellulase; operation at a compromise temperature of 37° C. is inefficient and prone to microbial contamination.

A third approach to overcoming the shortage of β-glucosidase is to use genetic engineering to overexpress the enzyme and increase its production by *Trichoderma*. This approach was taken by Barnett, Berka, and Fowler, in "Cloning and Amplification of the Gene Encoding an Extracellular B-glucosidase from *Trichoderma reesei*: Evidence for Improved Rates of Saccharification of Cellulosic Substrates," BioTechnology, Volume 9, June 1991, p. 562–567, herein referred to as "Barrett, et al."; and Fowler, Barnett, and Shoemaker in WO 92/10581, "Improved Saccharification of Cellulose by Cloning and Amplification of the B-glucosidase gene of *Trichoderma reesei*," herein referred to as Fowler, et al."

Both Barnett, et al. and Fowler, et al. describe the insertion of multiple copies of the β-glucosidase gene into *Trichoderma reesei* strain P40. Both groups constructed plasmid pSASβ-glu, a transformation vector containing the genomic *T. reesei* β-glucosidase gene and the amdS selectable marker. The amdS gene is from *Aspergillus nidulans* and codes for the enzyme acetamidase, which allows transformed cells to grow on acetamide as a sole source of nitrogen. *T. reesei* does not contain a functional equivalent to the amdS gene and is therefore unable to utilize acetamide as a nitrogen source. The transformed cells contained 10 to 15 copies of the β-glucosidase gene and produced 5.5-fold more β-glucosidase than the untransformed cells.

The enhanced production of β-glucosidase obtained by Barnett, et al. and Fowler, et al. is not sufficient to alleviate the shortage of β-glucosidase for cellulose hydrolysis. The amount of β-glucosidase made by natural *Trichoderma* strains, for example, must be increased at least 10-fold to meet the requirements of cellulose hydrolysis.

When overexpressing proteins in *Trichoderma*, one strategy is to link the gene of interest directly to the cbh1 promoter or to the cbh1 secretion signal. Since CBH1 is the most abundant protein produced by *Trichoderma* under cellulase-inducing conditions, the cbh1 promoter and secretion signal are thought to be very effective in directing the transcription and secretion of proteins encoded by a gene positioned after them in a genetic construct. Such a strategy has been successfully used to overexpress proteins from *Trichoderma* and other microorganisms (Margolles-Clark, Hayes, Harman and Penttila, 1996, "Improved Production of *Trichoderma harzianum* endochitinase by expression in *Trichoderma reesei*", Appl. Environ. Microbiol. 62(6): 2145–2151; Joutsjouki, Torkkeli and Nevalainen, 1993, "Transformation of *Trichoderma reesei* with the *Hormoconis resinae* glucoamylase P (gamP) gene: production of a heterologous glucoamylase by *Trichoderma reesei*", Curr. Genet. 24: 223–228; Karhunen, Mantyla, Nevalainen and Suominen, 1993, "High frequency one-step gene replacement in *Trichoderma reesei* 1. Endoglucanase I overproduction", Mol. Gen. Genet. 241: 515–522).

Another example of an industrial enzyme produced within fungal expression systems includes xylanase. Some of the most important commercial xylanases are classified as Family 11 xylanases. A xylanase enzyme is classified in Family 11 if it possesses the amino acids common to Family 11, including two glutamic acid residues serving as the essential catalytic residues. These residues are amino acids 86 and 177 by *Trichoderma reesei* xylanase II numbering. The amino acids common to Family 11 xylanases are described in Wakarchuck, et al, Protein Science 3:467–475 (1994).

The expression of pharmaceutically important heterologous proteins, for example insulin (Goeddel D. V. et al., 1979, Proc. Nat. Acad. Sci. 76 106–110), and blood coagulation factor $X_a$ (Smith D. B. 1988, Gene 67: 31–40), have been reported using bacterial expression systems. Similarly, U.S. Pat. No. 4,751,180 discloses the expression of a heterologous protein in yeast, including insulin and IgF-2.

The heterologous production of bovine prochymosin has been reported using the filamentous fungi *Trichoderma reesei* (Harkki A. et al., 1989, Bio/Technol. 7:596–603), with the genetic construct comprising a cbh1 (cellobiohydrolase I gene) regulatory region and terminator, either the cbh1 or the chymosin signal sequence, and optionally an intervening region obtained from cbh1. Margolles-Clark E. et al., (1996, App Environ Microbiol., 62:2152–2155) disclose the expression of *T. haraianum* endochitinase using cbh1 promoter from *T. reesei*. Similarly, proteins of interest, for example chymosin, have also been produced in the filamentous fungi *Aspergillus nidulans* and *A. awamori*, using genetic constructs comprising the regulatory region and secretion signal from the glaA (glucoamylase) gene, a signal sequence from either glaA or chymosin, and an intervening region from glucoamylase (EP 215,594). In both of these latter cases, transcription of the protein product within the host was not a limiting factor of heterologous protein production. However, secretion of the protein product out of the host was low and resulted in poor extracellular protein recovery.

In an attempt to increase the extracellular accumulation of heterologous protein production within a filamentous fungi expression system, Lawlis (1997, U.S. Pat. No. 5,679,543) disclosed the use of a multi-component fusion polypeptide to enhance secretion and extracellular accumulation of a protein of interest. The genetic constructs were complex encoding a fusion protein comprising four parts and included a signal peptide, a secreted polypeptide or portion thereof (a carrier protein), a clevable linker polypeptide, and the desired polypeptide for which expression is desired. Increased levels of protein secretion were attributed to the use of a glaA signal sequence fused to full length glucoamylase (the carrier protein), or other protein that is secreted within the host, which was then fused to the cleavable linker and protein of interest (chymosin). Such construct were found to increase the secretion of the fusion polypeptide when expressed in the filamentous fungi *A. nidulans*.

Even though increased secretion was noted within U.S. Pat. No. 5,679,543, using these four-component fusion proteins, the production of the expression vectors is complex. This expression system requires the use of a six-part genetic construct that expresses a complex four-part protein product with an expressed and variable carrier protein. Furthermore, approximately 50% of the desired expressed product is not recovered as it comprises the carrier protein, and this increases costs associated with post expression handling and purification of the desired protein. Significant post-secretion processing including linker cleavage and acidification of the medium is also required for recovery of the desired final protein product.

There is required within the art a simplified expression system that results in high levels of expression and secretion of a protein of interest from a host cell. Preferably, the genetic constructs used within this expression system comprise few component parts, so that the chimeric construct is easy to prepare. Furthermore, the levels of expression and secretion using such genetic construct should be high, and preferably, little or no downstream manipulations are required for harvesting the protein of interest.

It is an object of the invention to overcome disadvantages of the prior art.

The above object is met by the combinations of features of the main claims, the sub-claims disclose further advantageous embodiments of the invention

SUMMARY OF THE INVENTION

The present invention relates to the genetic modification of fungi to enhance production of a protein of interest. Furthermore, this invention relates to novel genetic constructs that dramatically increase the amount of protein produced and secreted by fungi containing these constructs. The genetic constructs of the present invention may be used to enhance the production of a protein of interest within fungal expression systems.

The genetic constructs that accomplish this task comprise DNA sequences that comprise one or more regulatory elements in operative association with a nucleotide sequence encoding a xylanase secretion signal, optionally an intervening region, and a protein of interest.

The present invention relates to a nucleotide sequence comprising, a regulatory region in operative association with a xylanase secretion sequence and a gene of interest, wherein at least one of the regulatory region, or gene of interest is not normally associated with the production of xylanase protein. An embodiment of this invention is also directed to the nucleotide sequence defined above, wherein the regulatory region is selected from the group consisting of cbh1, cbh2, eg1, eg2, eg3, eg5, xln1, and xln2.

The present invention also pertains to the nucleotide sequence as defined above wherein the gene interest is selected from a gene encoding a protein selected from the group consisting of a pharmaceutical, nutraceutical, industrial, an animal feed, a food supplement, or an enzyme. Preferably, the gene of interest encodes an enzyme selected from the group consisting of a β-glucosidase, cellulase, hemicellulase, a lignin degrading enzyme, protease, pectinase, and peroxidase.

The nucleotide sequence of the present invention as defined above may further comprising an intervening sequence.

This invention also pertains to a vector comprising the nucleotide sequence as described above, and to a transformed filamentous fungi comprising this vector. This invention also pertains to a filamentous fungi comprising the nucleotide sequence as defined above. Preferably, the transformed filamentous fungi is selected from the group consisting of *Trichoderma, Humicola, Fusarium, Aspergillus, Botrytis, Mycogone, Verticillium, Streptomyces, Colletotrichum, Neurospora, Pleurotus, Penicillum, Cephalosporium, Myrothecium, Papulospora, Achlya, Podospora, Endothia, Mucor, Cochilobbolus, Tolypocladium, Pyricularia, Penicillium, Myceliophthora, Irpex, Stachybotrys, Scorpulariopsis, Chaetomium, Gilocladium, Cephalosporin* and *Acremonium*.

This invention embraces a method of producing a protein of interest within a filamentous fungi comprising, transforming the filamentous fungi with a nucleic acid sequence comprising, a regulatory region in operative association with a xylanase secretion sequence and a gene of interest, wherein at least one of the regulatory region, or gene of interest is not normally associated with the production of xylanase protein, and wherein the xylanase secretion sequence is heterologous or homologous with respect to the filamentous fungi, growing the filamentous fungi, and causing the fungi to produce the protein of interest. Optionally, the protein of interest may be purified.

This invention is directed to method of producing a protein of interest within a filamentous fungi comprising, transforming the filamentous fungi with a nucleic acid sequence comprising, a regulatory region in operative association with a xylanase secretion sequence, an intervening sequence, and a gene of interest, wherein at least one of the regulatory region, or gene of interest is not normally associated with the production of xylanase protein, and wherein the xylanase secretion sequence is heterologous or homologous with respect to the filamentous fungi, growing the filamentous fungi, and causing the fungi to produce the protein of interest. Optionally, the protein of interest may be purified. Furthermore, the amino acid sequence encoded by the intervening sequence may be removed from the protein of interest.

The present invention also pertains to a protein produced by the methods as described above.

As disclosed herein, the use of the xylanase secretion signal resulted in higher levels of expression and secretion of a range of proteins of interest than the use of prior art secretion signals, for example a cbh1 secretion signal. Since xylanase comprises a much smaller proportion of the total protein produced by *Trichoderma* than does CBH1 (5% and 60%, respectively), one would expect that the cbh1 secretion signal would be more effective, however, this is not the case. Furthermore, the xylanase secretion signal enhanced protein production in several host expression systems.

This summary of the invention does not necessarily describe all necessary features of the invention but that the invention may also reside in a sub-combination of the described features.

Other aspects of our invention will be better understood and advantages thereof more apparent in view of the following detailed description of the preferred embodiments and accompanying drawings.

BRIEF DESCRIPTION OF THE DRAWINGS

FIG. 7: Shows schematic maps of man1 expression vectors pCMAN-TV (FIG. 7a) as described in Example 27. FIG. 7b shows the map of pXMAN-TV.

FIG. 8: Shows schematic maps of expression vectors comprising eg2 obtained from *Humicola insolens*. FIG. 8a shows pChHE2-TV, and FIG. 8b pC/XhHE2-TV, comprising the xln2 secretion signal, are both described in Example 30.

FIG. 9: Shows schematic maps of laccase I (lcc1) expression vectors.

DETAILED DESCRIPTION OF THE PREFERRED EMBODIMENTS

Figure 1:
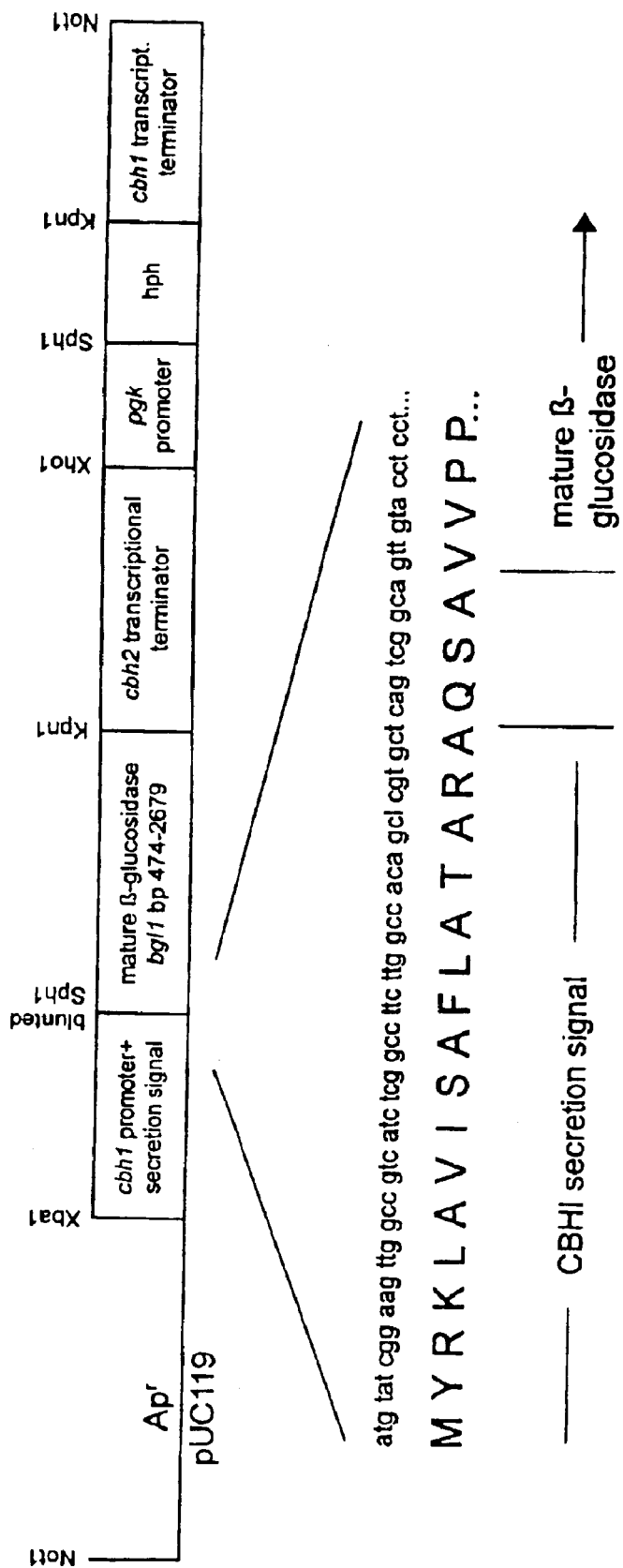
FIG. 1: Restriction map of the vector pCBG1-TV and the amino acid sequences of the CBH1 secretion signal/mature β-glucosidase juncture SEQ. ID NO.: 1, SEQ. ID NO.: 2 (see Example 5).

This invention relates to genetic modification of fungi to enhance production of a protein of interest. Furthermore, this invention relates to novel genetic constructs that dramatically increase the amount of protein produced by fungi containing these constructs.

The following description is of a preferred embodiment by way of example only and without limitation to the combination of features necessary for carrying the invention into effect.

The genetic modification of fungi as described in the present invention arises from the use of novel genetic constructs used for the expression of a gene of interest. The gene of interest encodes a protein of interest which is expressed at high levels within the host, and furthermore, is secreted from the host. The preferred expression host is a filamentous fungi. Filamentous fungi are characterized by a vegetative mycellium exhibiting a cell wall comprised of complex polysaccharides including chitin and cellulose. Vegetative growth typically proceeds through hyphal elongation. Examples of filamentous fungi that may be used within the present invention include, but are not limited to, *Trichoderma, Humicola, Fusarium, Aspergillus, Botrytis, Mycogone, Verticillium, Streptomyces, Colletotrichum, Neurospora, Pleurotus, Penicillum, Cephalosporium,*

*Myrothecium, Papulospora, Achlya, Podospora, Endothia, Mucor, Cochilobbolus, Tolypocladium, Pyricularia, Penicillium, Myceliophthora, Irpex, Stachybotrys, Scorpulariopsis, Chaetomium, Gilocladium, Cephalosporin* and *Acremonium*. Methods for the transformation of filamentous fungi are known in the art (e.g. EP 870,835; U.S. Pat. No. 5,863,783; Camels T. et al. Curr Genet., 1991, 20:309–314; Lorito et al., 1993, Curr. Genet. 24: 349–356; Goldman et al., 1990, Curr. Genet. 17:169–174; Penttila, et al. 1987, Gene 6: 155–164; Yelton et al.,1984, Proc. Natl. Acad. Sci. USA 81:1470–1474; Bajar et al., 1991, Proc. Natl. Acad. Sci. USA 88:8202–8212; Hopwood et al., 1985, "Genetic Manipulation of *Streptomyces*: a laboratory manual," The John Innes Foundation, Norwich, UK; all of which are incorporated herein by reference).

The genetic constructs of the present invention typically comprises a regulatory region, in operative association with a secretion signal and a gene of interest, and other elements, for example terminator sequences, markers etc. that may be added as required. An intervening sequence between the secretion signal and a gene of interest may be used if desired.

The Regulatory Region

By "regulatory region" or "regulatory element" it is meant a portion of nucleic acid typically, but not always, upstream of a gene, which is typically comprised of DNA. A regulatory element includes promoter elements, basal (core) promoter elements, elements that are inducible in response to an external stimulus, elements that mediate promoter activity such as negative regulatory elements or transcriptional enhancers. Regulatory element, as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region. In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, for example but not limited to those located 3' of the sequence, may also contribute to the regulation of expression of a coding region of interest. An example of a regulatory element that provides for the recognition for RNA polymerase or other transcriptional factors to ensure initiation at a particular site is a promoter element. A promoter element comprises a basal promoter element, responsible for the initiation of transcription, as well as other regulatory elements (as listed above) that modify gene expression.

Regulatory elements, as used herein, include developmentally regulated, inducible and constitutive regulatory elements. A regulatory element that is developmentally regulated, or controls the differential expression of a gene under its control, is activated at specific times during the development of the host. An inducible regulatory element is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory element to activate transcription, is present in an inactive form which is then directly or indirectly converted to the active form by the inducer. The inducer can be a chemical agent such as a protein, metabolite, or other chemical agent. A constitutive regulatory element directs the expression of a gene in a continuous manner throughout the host.

There are many suitable regulatory elements that have been cloned and characterized, and that may be used to drive the expression of a gene of interest within a fungal host as described herein. For example, which are not to be considered limiting in any manner, several genes and their associated regulatory regions have been cloned: EGIII from *T. reesei* (Saloheimo M et al., 1988, Gene 63: 11–21), xylanase, xln2 (Saarelainen et al. Mol. Gen. Genet. 241: 497–503, 1993). The use of other regulatory regions for the expression of heterologous genes of interest are also known within the art. For example, which are not to be considered limiting in any manner, the constitutive promoter pgk (phosphoglycerate kinase; Vanhanen et al., Gene 106: 129–133, 1991), the constitutive promoter pki obtained from *T. reesei* (Carmen LM et al., 1999, Phytopathol. 89;2554–261), the regulatory region obtained from carboxyl protease from *Mucor miehei* (U.S. Pat. No. 5,679,543), glaA (amyloglucosidase) Cullen D. et al., 1987, Bio/Technol. 5:713–719), gpd (glyceraldehyde-3-phosphate dehydrogenase) obtained from *Aspergillus* (Deane et al., 1999, Enzyme and Microbial Tech. vol 24, pp.419–424; Pentilla et al., 1987, Gene vol 61, pp. 155–164), tpiA from *A. nidulans* (McKinight, G. L. et al., 1986, Cell 46: 143–147), alcA from *Aspergillus* (Lockington, R. A., et al., 1986, Gene 33:137–149), amy (α-amylase) from *A. oryzae* (Christensen T. et al. 1988, Bio/Technol. 6:1419–1422), Tr1 from *T. reesei* (Camels et al (1991, Curr Genet. vol 20, pp. 309–314), cbh1 from *T. reesei* (Harkki, A. et al., 1989, Bio/Technol. 7:596–603), the regulatory region from glucoamlyase of *Aspergillus niger* (Nunberg J. H. et al., 1984, Mol. Cell. Bio. 4: 2306–2315; Boel E. et al., 1984, EMBO J., 3: 1581–1585), trpC from *A.* from *A. nidulans* (Yelton M. et al., 1984, Proc. Nat. Acad. Sci. 81: 1470–1474), xln1 or xln2 (Torronen et al., 1992, Bio/Technol. 10:1461–1465) or amdS from *A. nidulans* (Hynes M. J., et al., 1983 Mol. Cell. Genet. 199: 3745). The use of heterologous regulatory elements, including xlnA, phytase, ATP-synthetase, subunit 9 (oliC), tpi (triose phosphate isomerase), adh (alcohol dehydrogenase) amy, glaA, lactase and gpd has also been described in U.S. Pat. No. 5,863,783

The practice of the present invention is not constrained by the choice of regulatory element used within the genetic construct. However, preferred regulatory elements are cbh1, cbh2, eg1, eg2, eg3, eg5, xln1 and xln2. The DNA sequence of the *Trichoderma reesei* cbh1 is deposited in GenBank under Accession Number D86235.

Those skilled in the art are aware that a natural regulatory element can be modified by replacement, substitution, addition or elimination of one or more nucleotides without changing its function. The practice of the invention encompasses and is not constrained by such alterations to the promoter.

A Secretion Signal.

A "secretion signal", which may also be referred to as a "secretory sequence" is used to enhance the extracellular localization of the protein of interest from the host. As described herein, the preferred secretion signal is a xylanase secretion signal obtained from xylanase. The xylanase secretion signal is the DNA sequence that encodes a xylanase secretion signal peptide. The xylanase secretion signal peptide (or secretory peptide) is the peptide sequence present at the amino terminus of the encoded xylanase enzyme that is subsequently removed during export of the mature xylanase enzyme out of the host cell. The secretion signal may comprise a pro-peptide, a pre-peptide or both.

In a preferred embodiment, the xylanase secretion signal comprises a xylanase secretion signal of a Family 11 xylanase gene. In a more preferred embodiment, the Family 11 xylanase gene is a *Trichoderma* xylanase gene. In an even more preferred embodiment, the xylanase secretion signal comprises a xylanase secretion signal of *Trichoderma* xylanase I (xln1) gene or xylanase II (xln2) gene. The DNA sequences of the *Trichoderma* xln1 and xln2 secretion signals can be found in FIGS. 3 and 2, respectively, of Torronen, Mach, Messner, Gonzalez, Kalkkinen, Harkki and Kubicek, "The two major xylanases from *Trichoderma reesei*: characterization of both enzymes and genes, Bio/Technology 10: 1461–1465, 1992 (the gene identifications in the figure legends, as published, are reversed).

Those skilled in the art are aware that a natural secretion signal can be modified by replacement, substitution, addition, or elimination of one or more nucleic acids without changing its function. The practice of the invention encompasses and is not constrained by such alterations to the xylanase secretion signal.

Intervening Region

Additional nucleotide sequences may be inserted within the intervening region between the signal sequence and the gene of interest. These sequences may be introduced for a variety of purposes, for example to increase the length of the leader polypeptide, to help in the ease of inserting the gene of interest within the genetic construct, to increase the level of expression of the protein of interest, to increase the export of the protein of interest from the host (e.g U.S. Pat. No. 5,679,543), or to help in the purification of the protein of interest, for example using affinity chromatography or other methods that are well known in the art. The leader sequence may be of variable length, from several amino acids to an amino acid sequence encoding a protein typically exported by the host. Further the leader sequence may also encode amino acids that help with the isolation of a protein of interest using a cleavable linker. The use of a cleavable linker may be desired if the intervening region comprises a leader polypeptide that affects the activity of the protein of interest, comprises an affinity tag used for protein purification, or if the leader polypeptide is of considerable length. Such cleavable linkers are well known in the art, for example, but not limited to the amino acid methionine, which is cleaved by cyanogen bromide, or amino acid sequences known to be cleaved by proteases, for example, but not limited to, trypsin, collagenase, clostripin, KEX2 protease from yeast, factor $X_a$, subtilisin (e.g Martson F. A. O. 1986, Biol. Chem J. 240:1–12). However, it is to be understood that genetic constructs of the present invention may also lack such intervening sequences.

The genetic constructs described in Examples 5–7, 23, 27, 28, 30, and 32 contain nine additional base pairs of DNA sequence as shown in FIGS. 1–3, and 6–9; the first three encode the glutamine residue after the secretion signal of the *Trichoderma reesei* xylanase II gene, and the remaining six result from the insertion and/or modification of unique restriction sites used to join the xylanase secretion signal to the nucleotide sequence encoding the protein of interest. These DNA sequences result in the presence of additional amino acids between the xylanase secretion signal peptide and the protein of interest. These DNA sequences, which may be natural or synthetic, may encode one or more of the amino acids of the mature xylanase protein corresponding to the xylanase secretion signal encoded by the construct or may result from the addition of restriction enzyme sites needed to join the xylanase secretion signal sequence to the gene of interest. The intervening sequence may also comprise nucleotides encoding amino acids cleaved by proteases, or leader polypeptides, as described above. The practice of the invention encompasses but is not constrained by the presence of additional DNA sequences between the xylanase secretion signal and the mature β-glucosidase coding region.

The Gene of Interest:

By "gene of interest" it is meant any gene that is to be expressed in a transformed host. A gene of interest comprises the nucleic acid sequence that encodes a protein of interest. A protein of interest may include, but is not limited to, a pharmaceutically active protein, for example growth factors, growth regulators, antibodies, antigens, their derivatives useful for immunization or vaccination and the like, interleukins, insulin, G-CSF, GM-CSF, hPG-CSF, M-CSF or combinations thereof, interferons, for example, interferon-α, interferon-β, interferon-τ, blood clotting factors, for example, Factor VIII, Factor IX, or tPA or combinations thereof. A gene of interest may also encode an industrial enzyme, for example for use within pulp and paper, textile modification, or ethanol production. The gene of interest may also encode a protein supplement, nutraceutical, or a value-added product for animal feed, food, or both feed and food use. Examples of such proteins include, but are not limited to enzymes, proteases, oxidases, phytases, chitinases, mannanases, laccases, invertases, lipases, cellulases, hemicellulases, lignin degrading enzymes, pectinases, xylanases, β-glucosidases, peroxidases etc. Analogs of a protein of interest may also be expressed within the chimeric genetic constructs of the present invention. These analogs are typically characterized as having alterations to the amino acid sequence such as insertions, deletions, or other variations such as allelic variations and the like.

The present invention is further directed to chimeric gene constructs containing a DNA of interest operatively linked to a regulatory element and secretory sequence of the present invention. Any gene of interest, can be used and manipulated according to the present invention to result in the expression of the protein of interest.

Other Elements

The genetic construct may contain a transcriptional terminator immediately downstream of the nucleotide sequence encoding the protein of interest. Any suitable transcriptional terminator may be used as would be known to one of skill within the art. The practice of this invention is not constrained by choice of transcriptional terminator. An example of a transcriptional terminator, which is not to be considered limiting in any manner is the transcriptional terminator downstream of the gene of interest. Suitable terminators are readily available to one of skill in the art, and may be obtained from at least the genes identified above (see "Regulatory region").

A terminator, which is not to be considered limiting in any manner is described in Examples 5–7, 23, 27, 28, 30, 32 and 34 comprises 1.9 kb of DNA 3' to the stop codon of the *Trichoderma* cbh2 gene. The DNA sequence of the first 553 base pairs of the *Trichoderma reesei* cbh2 transcriptional terminator, which are located immediately downstream (or 3') of the TAA stop codon, is disclosed (see FIG. 2) Chen, Gritzali and Stafford, "Nucleotide Sequence and Deduced Primary Structure of Cellobiohydrolase II from *Trichoderma reesei*," Bio/Technology 5: 274–278, 1987. However, it is to be understood that other terminator sequences, for example but not limited to those obtained from cbh1, xln2 as disclosed in Examples 23, 27, and 28 (FIGS. 6a and 7a–c).

The genetic construct contains a selectable marker which may be present upstream or downstream of the genetic construct (i.e., at the 5' or 3' end of the construct) on the same plasmid vector or may be cotransformed with the construct on a separate plasmid vector. Choices of selectable markers are well known to those skilled in the art and include genes (synthetic or natural) that confer to the transformed cells the ability to utilize a metabolite that is not normally metabolized by the microbe (e.g., the *A. nidulans* amdS gene encoding acetamidase and conferring the ability to grow on acetamide as the sole nitrogen source) or antibiotic resistance (e.g., the *Escherichia coli* hph gene encoding hygromycin-β-phosphotransferase and conferring resistance to hygromycin). If the host strain lacks a functional gene for the marker chosen, then that gene may be used as a marker. Examples of such markers include trp, pyr4, pyrG, argB, leu, and the like. The corresponding host strain would therefore have to lack a functional gene corresponding to the marker chosen, i.e., trp, pyr, arg, leu and the like. The selectable marker used in the genetic constructs described in Examples 5–7, 27 and 28 is the *E. coli* hph gene expressed from the *Trichoderma* phosphoglycerate kinase (pgk) promoter. The use of pyr4 is disclosed in Examples 23, 30 and 32 (FIGS. 6b, 8a, 8b, 9a and 9b).

Figure 2:
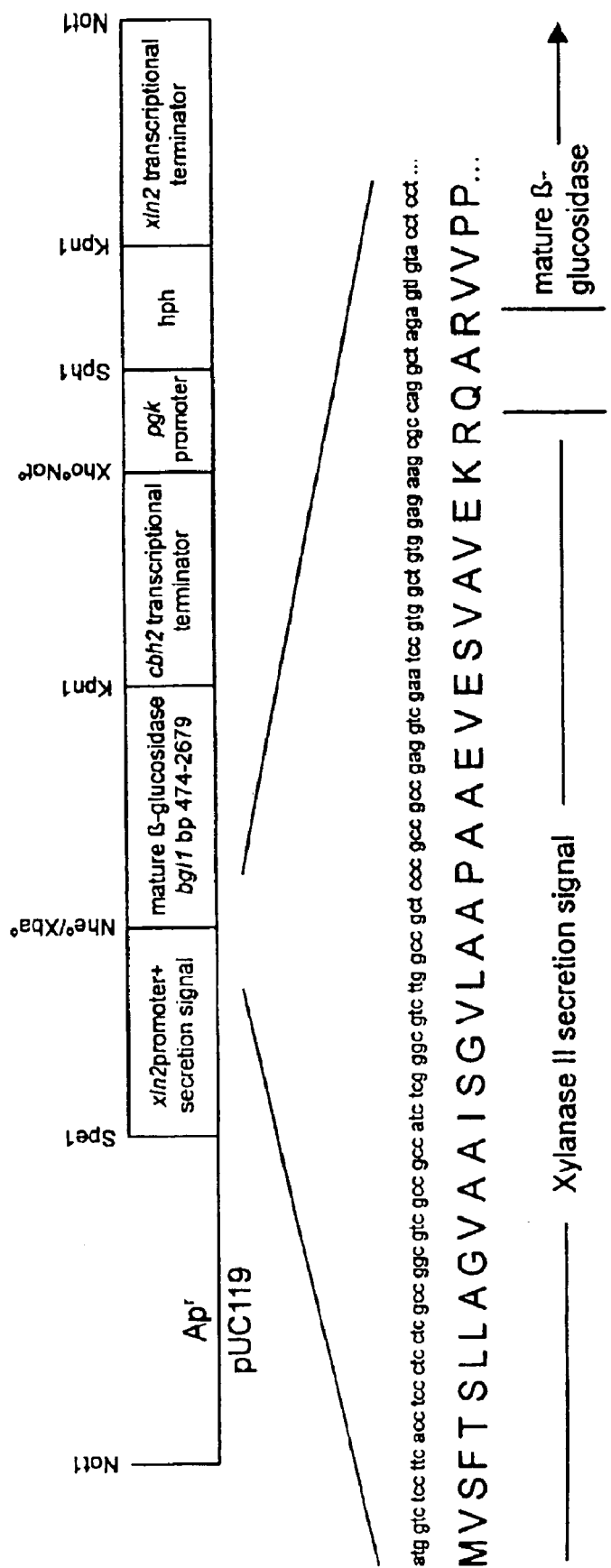
FIG. 2: Restriction map of the vector pXBG1-TV and the amino acid sequence of the xylanase II secretion signal/ mature β-glucosidase juncture SEQ. ID NO.: 3, SEQ. ID NO.: 4 (see Example 6).
Figure 4:
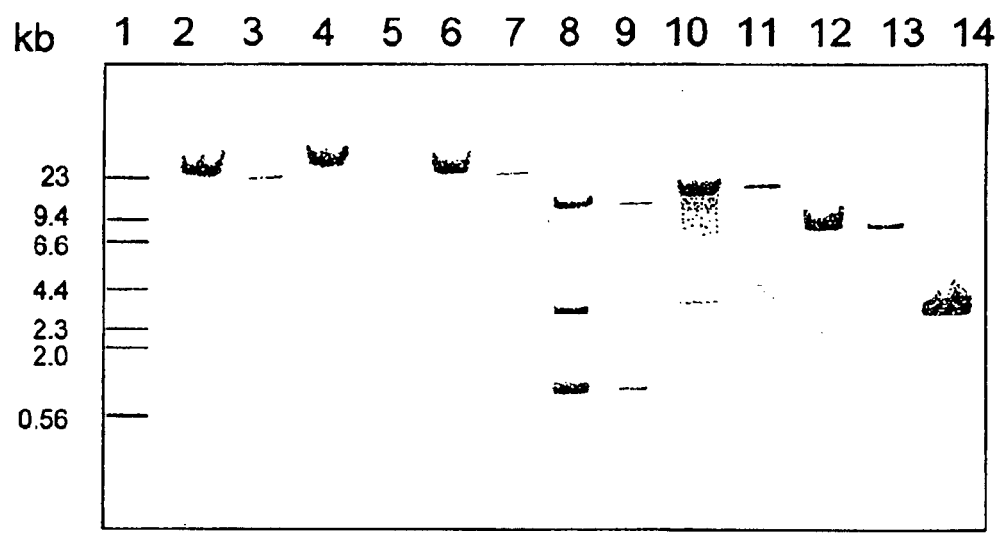
FIG. 4: Southern blot of genomic DNA isolated from *T. reesei* strains RutC30 and M2C38 and probed with a labeled DNA fragment comprising the M2C38 xylanase promoter plus secretion signal.

The DNA sequence of the *E. coli* hph gene can be found in FIG. 4 of Gritz and Davies, "Plasmid-encoded hygromycin B resistance: the sequence of hygromycin B phosphotransferase gene and its expression in *Escherichia coli* and *Saccharomyces cerevisiae*," Gene 25: 179–188, 1983; the DNA sequence of the *Trichoderma reesei* pgk promoter can be found in FIG. 2 of Vanhanen, Saloheimo, Ilmen, Knowles and Penttila, "Promoter structure and expression of the 3-phosphoglycerate kinase-encoding gene (pgk1) of *Trichoderma reesei*," Gene 106: 129–133 1991.

Therefore, the genetic constructs of the present invention comprise, a regulatory region in operative association with a xylanase secretion sequence and a gene of interest. Preferably, at least one of the regulatory region, or gene of interest is not normally associated with the production of xylanase protein.

One embodiment of the invention comprises the β-glucosidase genetic construct described thus far. The practice of our invention is not constrained by the method of making the construct, which can include, but is not restricted to, standard molecular biology techniques such as isolation of plasmid DNA from *E. coli* by alkaline lysis, digestion of plasmid DNA with restriction endonucleases, separation and isolation of DNA fragments by agarose gel electrophoresis, ligation of DNA fragments with T4 DNA ligase, insertion of unique restriction sites at the ends of DNA fragments by polymerase chain reaction or the addition of oligonucleotide linkers, and the blunting of DNA fragments with T4 DNA polymerase or Klenow fragment of *E. coli* DNA polymerase I.

Examples 1–7 describe procedures for making such genetic constructs.

The present invention also discloses the preparation of genetic constructs (expression vectors) comprising *T. reesei* and *H. insolens* endoglucanase II, eg2, (Examples 4, and 30), mannanase, man1, (Examples 27 and 28), laccase, lcc1, (Example 34) and xylanase (Example 38). The expression of several of these proteins of interest within *T. reesei* is described in Examples 25, 29, 31 and 33. The expression of a protein of interest *Humicola insolens* is described in Example 38.

In another embodiment of the present invention, the genetic construct encoding β-glucosidase, endoglucanaseII, mannaanse, laccase or xylanase is introduced into and expressed in a fungal host to create a genetically modified microbe. The resulting genetically modified microbe produces an increased level of the protein of interest relative to the untransformed microbial host, or when compared with transformed the host comprising a secretion signal that is endogenous to the gene being expressed. For all proteins of interest examined, and for all hosts examined, the chimeric genetic construct comprising the xylanase secretion signal resulted in increased amounts of the protein of interest being isolated from the host. For example, which is not to be considered limiting, increased level of β-glucosidase of preferably at least about 10-fold relative to the untransformed microbial host, more preferably at least about 40-fold relative to the untransformed microbial host, and most preferably at least about 120-fold relative to the untransformed microbial host were observed. Increased levels of expression were also observed with the other proteins of interest (see Examples 25, 29, 33, and 38 for expression of endoglucanase II, mannanse, laccase, and xylanase respectively).

This invention encompasses any method of introducing the genetic construct comprising the gene of interest into the microbial host familiar to those skilled in the art, including but not limited to, calcium chloride treatment of bacterial cells or fungal protoplasts to weaken the cell membranes, addition of polyethylene glycol to allow for fusion of cell membranes, depolarization of cell membranes by electroporation, *Agrobacterium* mediated transformation, shooting the DNA through the cell wall and membranes via microprojectile bombardment with a particle gun etc. Methods for the transformation of filamentous fungi have been reported (e.g. EP 870,835; U.S. Pat. No. 5,863,783; Camels T. et al. Curr Genet., 1991, 20:309–314; which are incorporated herein by reference)

Examples 9, 20 and 35 describe the procedures for introducing the β-glucosidase genetic construct into *Trichoderma* or *Humicola insolens* spores using a particle gun.

A 10-fold, or greater, enhancement of β-glucosidase production relative to the untransformed microbial host reflects a significant enhancement that is well above the natural variability of the strain and commercially significant. The degree of enhancement of β-glucosidase by this method has been as high as 136-fold and could reach over 1000-fold. The measurement of the degree of enhancement of β-glucosidase production is by growth of the culture and measurement of the β-glucosidase activity, as described in Example 11.

It is understood by those skilled in the art that the specific β-glucosidase activity of an enzyme mixture (in IU/mg protein) can be increased by decreasing the amount of cellulase and other proteins in the enzyme mixture. This can be done by physical and mechanical separations of the enzyme mixture or by deletion of the cellulase or other genes by recombinant means. Such methods have little or no effect on the actual production of β-glucosidase by the microorganism. These procedures may, however, be optionally included in the practice of our invention.

Examples 25, 29 and 33 describe the overexpression of endoglucanase II, mannase, and laccase using the chimeric constructs of the present invention. In all cases an increased level of production of the protein of interest was observed which varied from about 3 to 10 fold or more, increase in activity over that of the untransformed host. Examples 30 and 31 describe the production of *Humicola insolens* endoglucanase II within *T. reesei*, which also resulted in an increased levels of production of endoglucanase II.

Examples 34–38 describe the production of a xylanase, obtained from *T. reesei*, and its expression within *Humicola insolens*. These Examples demonstrate that a non-native promoter and secretion signal are active in a heterologous filamentous fungi, and that these elements drive the expression of a gene of interest which is active within a heterologous host. In these examples, the gene of interest was obtained from *Trichoderma* and encodes xylanase, it was fused to a xylanase secretion signal also obtained from *Trichoderma*. This nucleic acid sequence was placed under the control of the cbh1 promoter which was also obtained from *Trichoderma*. The final construct was used to transform *Humicola insolens*. The activities of the gene of interest within transformed and non-transformed *H. insolens* were determined (see Example 38) and demonstrate that the cbh1 promoter and xylanase secretion signal obtained from *Trichoderma* are active in *H. insolens*. Furthermore, the transformed host produces a 2 to 2.5 fold increase in activity over the endogenous activity expressed within the non-transformed host. The result of this experiment indicates that a non-native promoter and secretion signal obtained from one filamentous fungi is active in another filamentous fungi.

The present invention is therefore directed to the expression of a gene of interest, and the production of a protein of interest with any filamentous fungi. For example, which is not to be considered limiting in any manner, the host may be selected from *Trichoderma, Humicola, Fusarium, Aspergillus, Streptomyces, Colletotrichum, Neurospora, Pleurotus, Penicillum, Cephalosporium, Achlya, Podospora, Endothia, Mucor, Cochilobbolus, Tolypocladium, Pyricularia*. The selection of appropriate host may depend upon which protein of interest is to be produced. Methods have been published for the introduction of DNA constructs into *Trichoderma* (Lorito, Hayes, DiPietro and Harman, 1993, "Biolistic Transformation of *Trichoderma harzianum* and *Gliocladium virens* using plasmid and genomic DNA," Curr. Genet. 24: 349–356; Goldman, VanMontagu and Herrera-Estrella, 1990, "Transformation of *Trichoderma harsianum* by high-voltage electric pulse", Curr. Genet. 17:169–174; Penttila, Nevalainen, Ratto, Salminen and Knowles, 1987, "A versatile transformation system for the cellulolytic fungus *Trichoderma reesei*", Gene 6: 155–164), *Aspergillus* (Yelton, Hamer and Timberlake, 1984, "Transformation of *Aspergillus nidulans* using a trpC plasmid," Proc. Natl. Acad. Sci. USA 81: 14701474), *Fusarium* (Bajar, Podila and Kolattukudy, 1991, "Identification of a fungal cutinase promoter that is inducible by a plant signal via a phosphorylated transacting factor," Proc. Natl. Acad. Sci. USA 88: 8202–8212), *Tolypocladium* (Camels T. et al. Curr Genet., 1991, 20:309–314). Furthermore EP 870,835 discloses a method for the transformation of a range of filamentous fungi, including *Aspergillus, Colletotrichum, Fusarium, Neurospora, Pleurotus* and *Trichoderma* using *Agrobacterium* mediated gene transfer.

In a preferred embodiment, the microbial host is *Trichoderma*. In a more preferred embodiment, the microbial host is *Trichoderma reesei*.

The genetic constructs used in these published transformation methods are similar to those described in Examples 5–7, 23, 27, 28, 30, 32 and 34 in that they contain a regulatory region in operative association with a protein coding region (which may encode a selectable marker) and a transcriptional terminator. In most cases, the genetic constructs are linked to a selectable marker gene.

In a preferred embodiment, the xylanase secretion signal is native to the microbial host from which the genetically modified microbe is derived (i.e., the source of the xylanase secretion signal is the same type of microbial host as the microbial host from which said genetically modified microbe is derived). However, any xylanase secretion signal may be used as described herein.

The protein of interest produced used the methods and genetic constructs as described herein may be used as a crude extract as obtained from the host, or the protein of interest may be partially, or extensively purified using methods that are well known within the an including centrifugation, salt and pH precipitation, size exclusion, ion, affinity chromatography etc. The purification of the protein of interest may be enhanced using a leader polypeptide comprising an affinity tag and the separation of the tagged protein of interest using a suitable affinity matrix. Such affinity tags, and their corresponding affinity matrices are well known in the art. Furthermore, a leader peptide encoded by an intervening sequence may be cleaved from the expressed protein of interest prior to, during or following processing of the protein of interest.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1 describes the isolation of genomic DNA from *Trichoderma reesei* strains RutC30, M2C38, BTR48 and the genetically modified derivatives of these strains. Examples 2–7 describe the construction of genomic DNA libraries, the cloning of various genes, and several genetic constructs from *Trichoderma reesei* strain M2C38. Examples 9 and 11–15 describe the transformation and expression of β-glucosidase genetic constructs in *Trichoderma reesei* strains M2C38, BTR48, and RutC30.

*Trichoderma reesei* strains M2C38 and BTR48 are proprietary strains of Iogen Corporation, and were derived from *Trichoderma reesei* RutC30 (ATCC 56765, Montenecourt and Eveleigh, 1979, "Selective isolation of high yielding cellulase mutants of *T. reesei*", Adv. Chem. Ser. 181: 289–301), which was in turn derived from *Trichoderma reesei* Qm6A (ATCC 13631 Mandels and Reese, 1957 "Induction of cellulose in *Trichoderma viride* as influenced by carbon sources and metals", J. Bacterial. 73: 269–278).

In Example 1 and subsequent Examples, restriction endonucleases, T4 DNA polymerase, T4 DNA ligase and Klenow fragment of *E. coli* DNA polymerase 1 were purchased from Gibco/BRL, New England Biolabs, Boehringer Mannheim or Pharmacia and used as recommended by the manufacturer. Pwo polymerase with proof-reading activity (Boehringer Mannheim) was used in all polymerasechain reactions (PCR) according to the manufacturer's protocol. Hygromycin B was purchased from CalBiochem.

Example 1

Isolation of *Trichoderma reesei* Genomic DNA

To isolate genomic DNA, 50 ml of Potato Dextrose Broth (Difco), was inoculated with *T. reesei* spores collected from a Potato Dextrose Agar plate with a sterile inoculation loop. The cultures were shaken at 200 rpm for 2–3 days at 28° C. The mycelia was filtered onto a sterile GFA glass microfibre filter (Whatman) and washed with cold, deionized water.

The fungal cakes were frozen in liquid nitrogen and crushed into a powder with a pre-chilled mortar and pestle; 0.5 g of powdered biomass were resuspended in 5 ml of 100 mM Tris, 50 mM EDTA, pH 7.5 plus 1% sodium dodecyl sulphate (SDS). The lysate was centrifuged (5000 g for 20 min. 4° C.) to pellet cell debris. The supernatant was extracted with 1 volume buffer (10 mM Tris, 1 mM EDTA, pH 8.0) saturated phenol followed by extraction with 1 volume of buffer-saturated phenol:chloroform:isoamyl alcohol (25:24:1) in order to remove soluble proteins. DNA was precipitated from the solution by adding 0.1 volume of 3M sodium acetate, pH 5.2 and 2.5 volumes of cold 95% ethanol. After incubating for at least 1 h at −20° C., the DNA was pelleted by centrifugation (5000 g for 20 min. 4° C.), rinsed with 10 ml 70% ethanol, air-dried and resuspended in 1 ml 10 mM Tris, 1 mM EDTA, pH8.0. RNA is digested by the addition of Rib-onuclease A (Boehringer Mannheim) added to a final concentration of 0.1 mg/ml and incubation at 37° C. for 1 hour. Sequential extractions with 1 volume of buffer-saturated phenol and 1 volume of buffer saturated phenol:chloroform:isoamyl alcohol (25:24:1) are used to remove the ribonuclease from the DNA solution. The DNA is again precipitated with 0.1 volume of 3M sodium acetate, pH 5.2 and 2.5 volumes of cold 95% ethanol, pelleted by centrifugation, rinsed with 70% ethanol, air-dried and resuspended in 50 µl of 10 mM Tris, 1 mM EDTA, pH 8.0. The concentration of DNA was determined by measuring the absorbance of the solution at 260nm (p. C1 in Sambrook, Fritsch and Maniatis, "Molecular Cloning: A Laboratory Manual, Second Edition", Cold Spring Harbor Press 1989, hereafter referred to as Sambrook et al.).

Example 2
Construction of T. reesei Genomic Libraries

Two plasmid libraries and one phage library were constructed using genomic DNA isolated from T. reesei strain M2C38. The plasmid libraries were constructed in the vector pUC119 (Viera and Messing, "Isolation of single-stranded plasmid DNA", Methods Enzymol. 153:3, 1987) as follows: 10 µg genomic DNA was digested for 20 hrs at 37° C. in a 100 µl volume with 2 units/µg of HindIII, BamHI or EcoRI restriction enzymes. The digested DNA was fractionated on a 0.75% agarose gel run in 0.04M Tris-acetate, 1 mM EDTA, and stained with ethidium bromide. Gel slices corresponding to the sizes of the genes of interest (based on published information and Southern blots) were excised and subjected to electro-elution to recover the DNA fragments (Sambrook et al., pp. 6.28–6.29). These enriched fractions of DNA were ligated into pUC119 in order to create gene libraries in ligation reactions containing 20–50 µg/ml DNA in a 2:1 molar ratio of vector:insert DNA, 1 mM ATP and 5 units T4 DNA ligase in a total volume of 10–15 al at 4° C. for 16 h. Escherichia coli strain HB101 was electroporated with the ligation reactions using the Cell Proator System (Gibco/BRL) following the manufacturer's protocol and transformants selected on LB agar containing 70 µg/ml amplicillin.

The phage library was constructed in the vector λ-DASH (Stratagene, Inc.) as follows: genomic DNA (3 µg) was digested with 2, 1, 0.5 and 0.2 units/,µg Bam HI for 1 hour at 37° C. to generate fragments 9–23 kB in size. The DNA from each digest was purified by extraction with 1 volume Tris-saturated phenol:choroform:isoamyl alcohol (25:24:1) followed by precipitation with 10 µl 3M sodium acetate, pH 5.2 and 250 pl 95% ethanol (−20° C.). The digested DNA was pelleted by microcentrifugation, rinsed with 0.5 ml cold 70% ethanol, airdried and resuspended in 10 µl sterile, deionized water. Enrichment of DNA fragments 9–23 kB in size was confirmed by agarose gel electrophoresis (0.8% agarose in 0.04 M Tris-acetate, 1 mM EDTA). Digested DNA (0.4 µg) was ligated to 1 µg λ-DASH arms predigested with BamHI (Stratagene) in a reaction containing 2 units T4 DNA ligase and 1 mM ATP in a total volume of 5 µl at 4° C. overnight. The ligation mix was packaged into phage particles using the GigaPack® II Gold packaging extracts (Stratagene) following the manufacturer's protocol. The library was titered using the E. coli host strain XL1-Blue MRA (P2) and found to contain $3 \times 10^5$ independent clones.

Example 3

Isolation of T. reesei M2C38 clones of the cellobiohydrolase I (cbh1), cellobiohydrolase II (cbh2) and β-glucosidase (bgl1) genes from the pUC119 libraries E. coli HB101 transformants harboring cbh1, cbh2 or ball clones from the recombinant pUC119-Hind III, -BamHI or -EcoRI libraries were identified by colony lift hybridization: $1–3 \times 10^4$ colonies were transferred onto HyBond™ nylon membranes (Amersham); membranes were placed colony-side up onto blotting paper (VWR 238) saturated with 0.5 M NaOH, 1 M NaCl for 5 min to lyse the bacterial cells and denature the DNA; the membranes were then neutralized by placing them colony-side up onto blotting paper (VWR 238) saturated with 1.5 M Tris, pH 7.5 plus 1 M NaCl for 5 min. The membranes were allowed to air-dry for 30 min and the DNA was then fixed to the membranes by baking at 80° C. for 2 h.

$^{32}$P-labelled probes were prepared by PCR amplification of short (0.7–1.5 kB) fragments of the bgl1, cbh1 and cbh2 coding regions from the enriched pool of Hind III, BamHI or EcoRI fragments, respectively, in a labeling reaction containing 10–50 ng target DNA, 0.2 mM each d(GCT)TP, 0.5 µM dATP, 20–40 µCi alpha-$^{32}$P-dATP, 10 pmole oligonucleotide primers and 0.5 units Taq polymerase in a total volume of 20 µl. The reaction was subjected to 6–7 cycles of amplification (95° C., 2 min 56° C., 1.5 min 70° C., 5 min). The amplified, $^{32}$P-labelled DNA was precipitated by the addition of 0.5 ml 10% (w/v) trichloroacetic acid and 0.5 mg yeast tRNA. The DNA was pelleted by microcentrifugation, washed twice with 1 ml 70% ethanol, air-dried and resuspended in 1M Tris pH7.5, 1 mM EDTA.

Nylon membranes onto which the recombinant pUC119 plasmids had been fixed were prehybridized in heat-sealed bags for 1 h at 60–65° C. in 1 M NaCl, 1% SDS, 50 mM Tris, 1 mM EDTA pH 7.5 with 100 µg/ml denatured sheared salmon sperm DNA. Hybridizations were performed in heat-sealed bags in the same buffer with only 50 µg/ml denatured sheared salmon sperm DNA and $5 \times 10^6 – 5 \times 10^7$ cpm of denatured bgl1, cbh1 or cbh2 probe for 16–20 h at 60–65° C. Membranes were washed once for 15 min with 1 M NaCl, 0.5% SDS at 60° C., twice for 15 min each with 0.3M NaCl, 0.5% SDS at 60° C. and once for 15 min with 0.03M NaCl, 0.5% SDS at 55° C. Membranes were again placed in heat-sealed bags and exposed to Kodak RP X-ray film for 16–48 h at −70° C. The X-ray film was developed following the manufacturer's protocols. Colonies giving strong or weak signals were picked and cultured in 2×YT media supplemented with 70 µg/ml ampicillin. Plasmid DNA was isolated from these cultures using the alkaline lysis method (Sambrook et al., pp. 1.25–1.28) and analyzed by restriction digest, Southern hybridization (Sambrook et al., pp. 9.38–9.44) and PCR analysis (Sambrook et al., pp. 14.18–14.19).

Clones carrying the bgl1 gene were identified by colony lift hybridization of the pUC119-Hind III library (Example 2) with a 1.0 kb bgl1 probe prepared using oligonucleotide primers designed to amplify bp 462–1403 of the published bgl1 sequence (Barrett et al.). A ball clone, pJEN200, was isolated containing a 6.0 kb Hind III fragment corresponding to the promoter, structural gene and termination sequences. Clones carrying the cbh1 gene were identified by colony lift hybridization of the pUC119-BamHI library with a 0.7 kb cbh1 probe prepared using oligonucleotide primers designed to amplify bp 597–1361 of the published cbh1 sequence (Shoemaker, Schweikart, Ladner, Gelfand, Kwok, Myambo and Innis, "Molecular cloning of exo-cellobiohydrolyase 1 derived from *Trichoderma reesei* strain L27", Bio/Technology 1: 691–696, 1983 hereafter referred to as Shoemaker et al.). A cbh1 clone, pCOR132, was isolated containing a 5.7 kb BamHI fragment corresponding to the promoter (4.7 kb) and 1 kb of the cbh1 structural gene. From this, a 2.5 kb EcoRI fragment containing the cbh1 promoter (2.1 kb) and 5' end of the cbh1 coding region (0.4 kb) was subcloned into pUC119 to generate pCB152. Clones carrying the cbh2 gene were identified by colony lift hybridization of the pUC119-EcoRI library with a 1.5 kb cbh2 probe prepared using oligonucleotide primers designed to amplify bp 580–2114 of the published cbh2 sequence (Chen, Gritzali and Stafford, "Nucleotide sequence and deduced primary structure of cellobiohydrolase II from *Trichoderma reesei*", Bio/Technology 5: 274–278, 1987, hereafter referred to as Chen et al.). A cbh2 clone, pZUK600, was isolated containing a 4.8 kb EcoRI fragment corresponding to the promoter (600 bp), structural gene (2.3 kb) and terminator (1.9 kbp).

Example 4

Cloning of *T. reesei* M2C38 cbh1 terminator, xylanase II (xln2) gene, phosphoglycerate kinase promoter (pgk p).

Digoxigen-11-dUTP labelled probes were prepared from PCR amplified coding regions of the cbh1, xln2 and pgk genes by random prime labeling using the DIG Labeling and Detection kit (Boehringer Mannheim) and following the manufacturer's protocols. Genomic clones containing the cbh1, xln2 and pgk genes were identified by plaque-lift hybridization of the λ-DASH library. For each gene of interest, 1×10⁴ clones were transferred to Nytran® (Schleicher and Schull) nylon membranes. The phage particles were lysed and the phage DNA denatured by placing the membranes plaque-side up on blotting paper (VWR238) saturated with 0.5 M NaOH, 1 M NaCl for 5 min; the membranes were then neutralized by placing them plaque-side up onto blotting paper (VWR238) saturated with 1.5 M Tris, pH 7.5 plus 1 M NaCl for 5 min the membranes were allowed to air-dry for 30 min and the DNA was then fixed to the membranes by baking at 80° C. for 2 h. The membranes were prehybridized in heat-sealed bags in a solution of 6×SSPE, 5× Denhardt's, 1% SDS plus 100 μg/ml denatured, sheared salmon sperm DNA at 65° C. for 2 h. The membranes were then hybridized in heat-sealed bags in the same solution containing 50 μg/ml denatured, sheared salmon sperm DNA and 0.5 μg of digoxigen-dUTP labelled probes at 65° C. overnight. The membranes were washed twice for 15 min in 2×SSPE, 0.1% SDS at RT, twice for 15 min in 0.2×SSPE, 0.1% SDS at 65° C. and once for 5 min in 2×SSPE. Positively hybridizing clones were identified by reaction with an anti-digoxigenin/alkaline phosphatase antibody conjugate, 5-bromo-4-chloro-3-indoyl phosphate and 4-nitro blue tetrazolium chloride (Boehringer Mannheim) following the manufacturer's protocol. Positively hybridizing clones were purified further by a second round of screening with the digoxigendUTP labeled probes. Individual clones were isolated and the phage DNA purified as described in Sambrook, et al. (1989) pp. 2.118–2.121 with the exception that the CsCl gradient step was replaced by extraction with 1 volume of phenol:choroform:isoamyl alcohol (25:24:1) and 1 volume of chloroform: isoamyl alcohol (24:1). The DNA was precipitated with 0.1 volume of 3M sodium acetate, and pH 5.2 and 2.5 volumes cold 95% ethanol. The precipitated phage DNA was washed with 0.5 ml cold 70% ethanol, air-dried and resuspended in 50 μl 10 mM Tris, 1 mM EDTA pH8.0. Restriction fragments containing the genes of interest were identified by restriction digests of the purified phage DNA and Southern blot hybridization (Sambrook et al., pp. 9.38–9.44) using the same digoxigen-dUTP labeled probes used to screen the λ-DASH library. The membranes were hybridized and positively hybridizing fragments visualized by the same methods used for the plaque lifts. Once the desired restriction fragments from each λ-DASH clone were identified, the restriction digests were repeated, the fragments were resolved on a 0.8% agarose gel in TAE and the desired bands excised. The DNA was eluted from the gel slices using the Sephaglas BandPrep Kit (Pharmacia) following the manufacturer's protocol.

Clones carrying the cbh1 gene were identified by colony lift hybridization of the λ-DASH library (example 2) with a cbh1 probe comprising bp 45–2220 of the published cbh1 sequence (Shoemaker et al.). A 1.8 kb BamHI fragment containing the 3' end of the cbh1 coding region (0.5 kb) and the cbh1 terminator (1.3 kb) was isolated by restriction digestion of phage DNA purified from a λ-DASH cbh1 clone. This fragment was subcloned into the BamHI site of the *E.coli* plasmid vector pUC119 to generate the plasmid pCBITa. Clones carrying the xln2 gene were identified by colony lift hybridization of the λ-DASH library (example 2) with a xln2 probe comprising bp 100–783 of the published xln2 sequence (Saarelainen, Paloheimo, Fagerstrom, Suominen and Nevalainen, "Cloning, sequencing and enhanced expression of the *Trichoderma reesei* endoxylanase II (pI 9) gene xln2", Mol. Gen. Genet. 241: 497–503, 1993, hereafter referred to as Saarelainen et al.). A 5.7 kb KpnI fragment containing the promoter (2.3 kb), coding region (0.8 kb) and terminator (2.6 kb) the xln2 gene was isolated by restriction digestion of phage DNA purified from a λ-DASH xln2 clone. This fragment was subcloned into the KpnI site of pUC119 to generate the plasmid pXYN2K-2. Clones carrying the pgk gene were identified by colony lift hybridization of the λ-DASH library (Example 2) with a pgk1 probe comprising bp 4–1586 of the published pgk sequence (Vanhanen, Penttila, Lehtovaara and Knowles, "Isolation and characterization of the 3phosphoglycerate kinase gene (pgk) from the filamentous fungus *Trichoderma reesei*", Curr. Genet. 15: 181–186, 1989). A 5.0 kb EcoRI fragment containing the promoter (2.9 kb), coding region (1.6 kb) and terminator (0.5 kb) of the pgk gene was isolated by restriction digestion of phage DNA purified from a λ-DASH pgk clone. This fragment was subcloned into the EcoRI site of pUC119 to generate the plasmid pGK5.0.

Example 5

Construction of β-glucosidase Overexpression Vector pCBG1-TV

This Example describes the construction of a vector containing the *Trichoderma* cellobiohydrolase I promoter and secretion signal and the mature β-glucosidase coding region.

A DNA fragment containing the bgl1 coding region minus the B-glucosidase secretion signal (bp 474–2679) was amplified by PCR from the pJEN200 template using primers homologous to the published bgl1 sequence containing either an SphI site 5' to Val32 of the encoded B-glucosidase or a KpnI site 3' to the bgl1 stop codon using Pwo polymerase. This amplified fragment was digested with SphI and KpnI and inserted into pCB219N digested with SphI and KpnI to generate pBgstrf. To make pCB219N, a cbh2 terminator fragment was amplified from the pZUK600 template using a primer homologous to bp 2226–2242 of the published 3' untranslated region of the cbh2 gene (Chen et al., 1987) containing a KpnI site at the 5' end and the pUC forward primer (Cat. No. 1224, New England Biolabs) which anneals downstream of the EcoRI site at the 3' end of cbh2 in pZUK600. This fragment was digested at the engineered KpnI and EcoRI sites and inserted into the corresponding sites of pUC119 to generate pCB219. An EcoRI-NotI adaptor (Cat. No. 35310-010, Gibco/BRL) was inserted into the unique EcoRI site of pCB219 to generate pCB219N. A fragment containing the cbh1 promoter and secretion signal was amplified from pCB152 using a cbh1 specific primer (bp 249–284 of the published cbh1 sequence, Shoemaker et al., 1983) containing a SphI site 3' to Ser19 of the encoded CBH1 and pUC forward primer (Cat. No. 1224, New England Biolabs) which anneals upstream of the EcoRI site at the 5' end of cbh1 in pCB 152. The cbh1 promoter+ secretion signal PCR product was digested with SphI and EcoRI and inserted into the corresponding sites in pBR322L (a derivative of pBR322 in which the region between the SphI and SalI sites was replaced with an SphI-NotI-SalI linker) to generate pBR322LCS. To make the expression cassette, the bgl1 coding region and cbh2 terminator were isolated from pBgstrf as a 4.1 kb SphI/NotI fragment and inserted into pBR322LCS digested with SphI and NotI. In order to maintain the correct reading frame at the juncture of the cbh1 secretion signal and the mature B-glucosidase, the resultant plasmid, pCBGstrf, was linearized at the unique SphI site and the SphI site was blunted with T4 DNA polymerase. The resulting plasmid, pCBG1, was then further modified by conversion of the unique NotI site at the 3' end of the cbh2 terminator to a unique XhoI site by the addition of XhoI linkers (Cat. No. 1073, New England Biolabs). The final plasmid, pCBG1-Xho, is the expression cassette plasmid.

The *E coli* hygromycin phosphotransferase gene (hph) used as a selectable marker for *T. reesei* was amplified with Pwo polymerase from the plasmid pVU1005 (Van den Wizen, Townsend, Lee and Bedbrook, "A chimaeric hygromycin resistance gene as a selectable marker in plant cells", Plant Mol. Biol. 5: 299–302, 1989). The primers were designed to introduce SphI and KpnI sites at the 5' and 3' ends of the hph coding region (bp 211–1236 of the published hph sequence, Gritz and Davies, "Plasmid-encoded hygromycin b resistance: the sequence of hygromycin B phosphotransferase gene and its expression in *Escherichia coli* and *Saccharomyces cerevisiae*" Gene 25: 179–188,1983), respectively. The PCR product was digested with SphI and KpnI and inserted into the corresponding sites in the polylinker region of pUC119. The resulting plasmid, pHPT100 was used as the starting plasmid for the construction of the selection cassette. Two new linker regions were introduced into this plasmid to facilitate the cloning of the promoter and terminator fragments. A HindIII-XbaI-XhoI-SphI linker was inserted between the HindIII and SphI sites as well as a KpnI-NotI-SacI linker which was inserted between the KpnI and SacI sites of pUC119 polylinker remaining in pHPT100. This construct was designated as pHPT102. The primers used to amplify the pgk promoter (Vanhanen, Saloheimo, Ilmen, Knowles and Penttila, "Promoter structure and expression of the 3-phosphoglycerate kinase gene (pgkI) of *Trichoderma reesei*", Gene 106: 129–133, 1991) were designed to introduce an XhoI site and a SphI site at positions −970 and +1 of the promoter respectively. These sites were subsequently used to insert the pgk promoter into the XhoI and SphI sites of pHPT102 to generate pHPT115. A 1.3 kb cbh1 terminator fragment was amplified with Pwo polymerase from pCBITa using a primer annealing to the 3' untranslated region of cbh1 (bp 1864–1899 of the published cbh1 sequence) containing a KpnI site at bp1877–1882 and the pUC reverse primer (Cat. No., 18432-013, Gibco/BRL) which anneals downstream of the EcoRI site at the 3' end of the cbh1 terminator in pCBITa. The cbh1 terminator PCR product was digested with KpnI and inserted into the unique KpnI site of pHPT115 to generate the selection cassette plasmid pHPT136.

To make the transformation vector, the expression cassette from pCBG1-Xho was isolated as a 5.6 kb XbaI/XhoI fragment and inserted between the unique XbaI and XhoI sites upstream of the selection cassette of pHPT136. The final transformation vector, pCBG1-TV, as depicted in FIG. 1, was introduced as a circular plasmid into *T. reesei* M2C38 via microprojectile bombardment as described below in Example 9.

Example 6
Construction of β-glucosidase Overexpression Vector pXBG1-TV

This Example describes the construction of a vector containing the *Trichoderma* xylanase II promoter and secretion signal, and the mature β-glucosidase coding region.

The β-glucosidase coding region (bp 474–2680) was amplified with Pwo polymerase from the genomic bgl1 clone pJEN200 using primer to insert a XbaI site directly upstream of bp 474 in the published bgl1 sequence (Barrett, et al.) and a KpnI site directly downstream of bp 2680. The blunt ended PCR product was inserted into the SmaI site of pUC118 to generate the plasmid designated as pBGm.s. Since the XbaI site was engineered to be immediately upstream of the start of the mature β-glucosidase at Val32, the cloned fragment did not include the β-glucosidase secretion signal. The plasmid pBGm.s was digested with XbaI and KpnI and the 2.2 kb fragment containing the bgl1 coding region minus the secretion signal was isolated and inserted into the XbaI and KpnI sites upstream of the cbh2 terminator in the plasmid pCB219N (described in Example 5, above) to yield the plasmid pBG2X. A 2.3 kb fragment containing the promoter and secretion signal of the xln2 gene (bp −2150 to +99 where +1 indicates the ATG start codon) was amplified with Pwo polymerase from the genomic xln2 subclone pXYN2K-2 using a xln2-specific primer containing a NheI site directly downstream of bp103 of the published xln2 sequence (Saarelainen et al.) and the pUC reverse primer (Cat. No. 18432-013, Gibco/BRL) which anneals upstream of the KpnI site at the 5' end of the xln2 gene. This xln2 PCR product was digested with EcoRI (which was amplified as part of the pUC119 polylinker from pXYN2K-2i and NheI and inserted into the plasmid pBR322L (described in example 5 above) to generate pBR322LXN. The EcoRI site of pBR322LXN was then blunted with Klenow, and SpeI linkers (Cat. No. 1086, New England Biolabs) were added to generate pBR322SpXN. The pBG2X plasmid was cut with XbaI and NotI and a 4.2 kb fragment, containing the bgl1 coding region followed by the cbh2 terminator, was isolated. This fragment was inserted into the plasmid pBR322SpXN cut with NheI and NotI (NheI and XbaI have compatible overhangs). This cloning resulted in the fusion of the xylanase secretion signal directly to the mature β-glucosidase creating the complete expression cassette pXBG-2.

The cbh1 terminator in the selection cassette plasmid pHPT136 described in Example 5, above, was replaced with a 2.6 kb KpnI fragment containing the xln2 transcriptional terminator. The xln2 terminator was amplified with Pwo polymerase from the genomic subclone pXYN2K-2 using a primer to introduce a KpnI site directly downstream of bp 780 of the published xln2 sequence (Saarelainen et al.) and the pUC forward primer (Cat. No. 18431-015, Gibco/BRL) which anneals downstream of the 3' end of the xln2 gene in pXYN2K-2. The xln2 terminator PCR product was digested with KpnI and ligated to a 5.1 kb KpnI fragment from pHPT136 containing the pgk promoted-hph gene in pUC119 to generate the selection cassette plasmid pHPT136X.

The construction of the transformation vector involved the insertion of the expression cassette directly upstream of the pgk promoter from the selection cassette. The expression cassette plasmid pXBG2 was digested with NotI, the ends were made blunt using Klenow, and then digested with SpeI. The selection cassette pHPT136X was prepared in a similar manner by digestion with XhoI, followed by the fill in reaction to create the blunt ends and then a digestion with XbaI. A blunt-sticky ligation of these two fragments was performed to ligate the 6.5 kb SpeI/blunted NotI fragment from pXBG2 into the XbaI/blunted XhoI fragment of pHPT136X (SpeI and XbaI have compatible overhangs). The final transformation vector, pXBG-TV, as depicted in FIG. 2, was linearized at its unique NotI prior to transformation of *T. reesei* M2C38 via microprojectile bombardment, as described below in Example 9.

Example 7

Construction of β-glucosidase Overexpression Vector pC/XBG(XbaI)-TV

This Example describes the construction of a vector containing the *Trichoderma* cellobiohydrolase 1 promoter, the xylanase II secretion signal and the mature β-glucosidase coding region.

Figure 3:
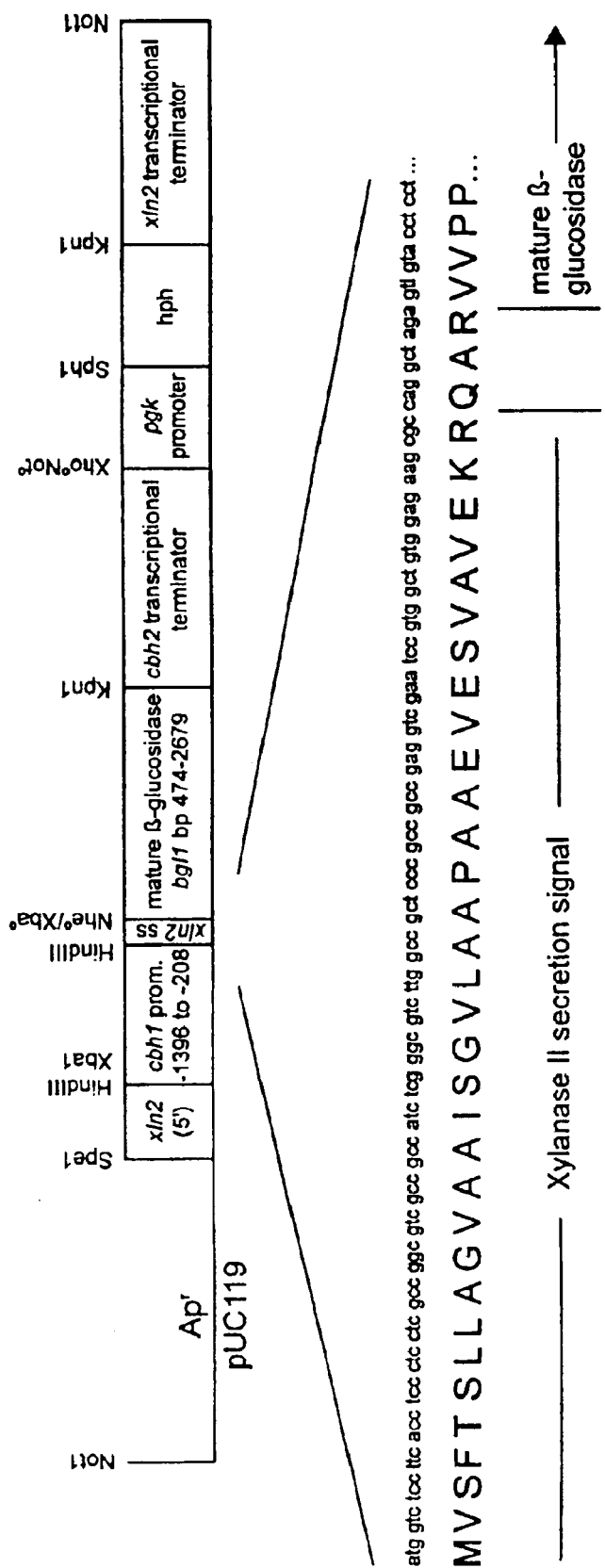
FIG. 3: Restriction map of the vector pC/XBG(XbaI)-TV and the amino acid sequence of the xylanase II secretion signal/mature β-glucosidase juncture SEQ. ID NO.: 3, SEQ. ID NO.: 4 (see Example 7).

This Example was carried out to test the combined effects of the cbh1 promoter and xln2 secretion signal on bgl expression. A 1.2 kb HindIII fragment comprising bp −1399 to −204 of the cbh1 promoter was amplified by PCR using the cbh1 promoter-containing plasmid pBR322LCS (Example 5) as a template in order to insert a unique XbaI site at bp −1393 to −1388. This modified cbh1 promoter fragment was digested with HindIII and was used to replace bp −1400 to −121 of the xln2 promoter in pXBG1 (Example 6) to generate the new expression cassette plasmid pC/XBG1. The 6.4 kb expression cassette from pC/XBG1 was isolated by digestion with NotI followed by blunting of the NotI site with Klenow fragment and subsequent digestion with SpeI. This fragment was then inserted by blunt/sticky ligation upstream of the hph selection cassette in pHPT136X which had been digested with XhoI, blunted at the XhoI site with Klenow and digested with XbaI. The final transformation vector, pC/XBG(XbaI)-TV (Accession No. 209613, deposit date Feb. 3, 1998, American Type Culture Collection, 12301 Parklawn Drive, Rockville, Md. 20852 USA), as shown in FIG. 3, was linearized at the unique XbaI and NotI sites at the 5' end of the cbh1 promoter and the 3' end of the xln2 terminator prior to transformation of *T. reesei* M2C38 v~a microprojectile bombardment, as described below in Example 9.

Example 8

Southern Blots of Genomic DNA Isolated from *T. reesei* Strains RutC30 and M2C38

Figure 5:
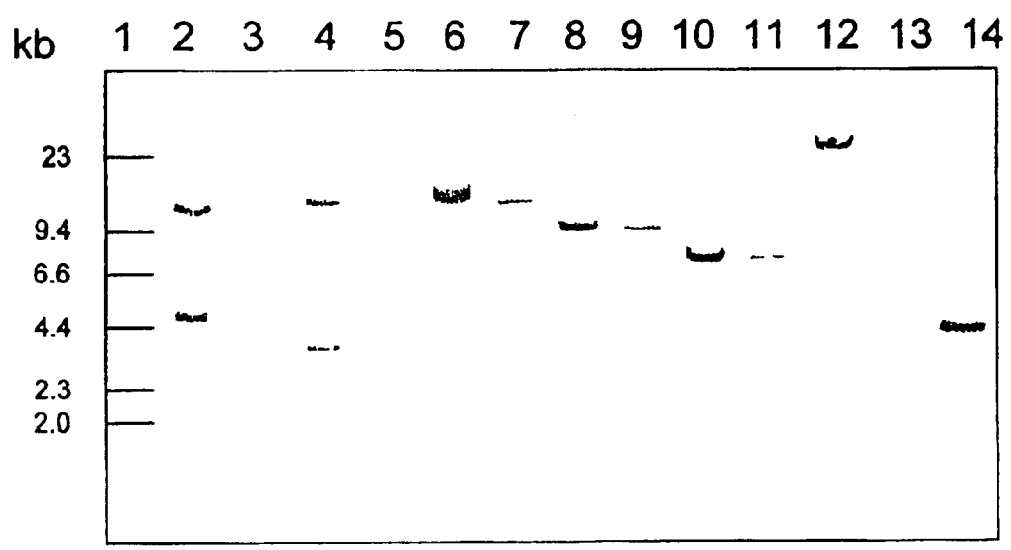
FIG. 5: Southern blot of genomic DNA isolated from *T. reesei* strains RutC30 and M2C38 and probed with a labeled DNA fragment comprising the M2C38 mature β-glucosidase coding region.
Figures 6A, 6B:
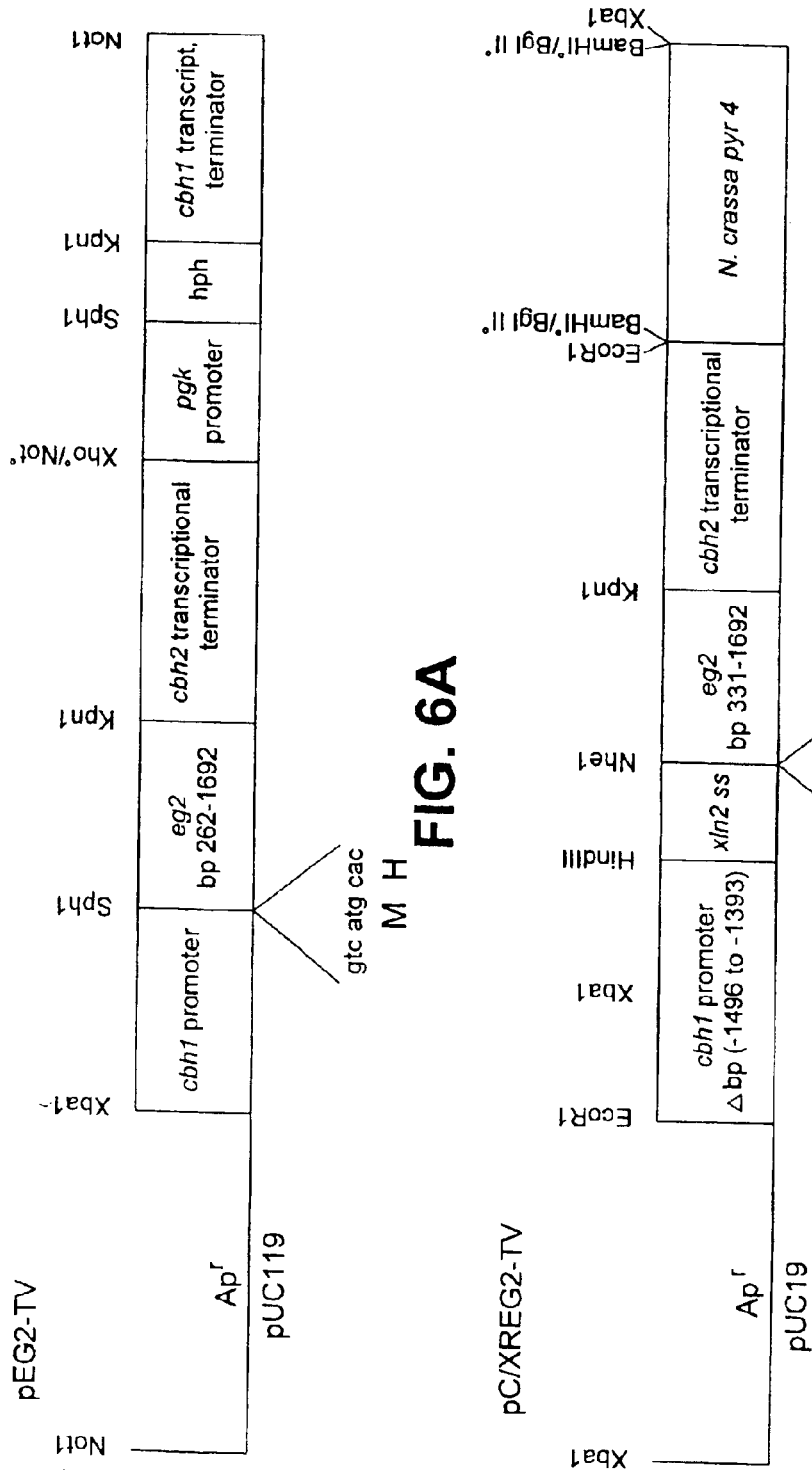
FIG. 6: Shows schematic maps of eg2 expression vectors, pEG2-TV (FIG. 6a) and pC/XREG2-TV (FIG. 6b), which comprises the xln2 secretion signal, as described in Example 23.
Figure 7C:
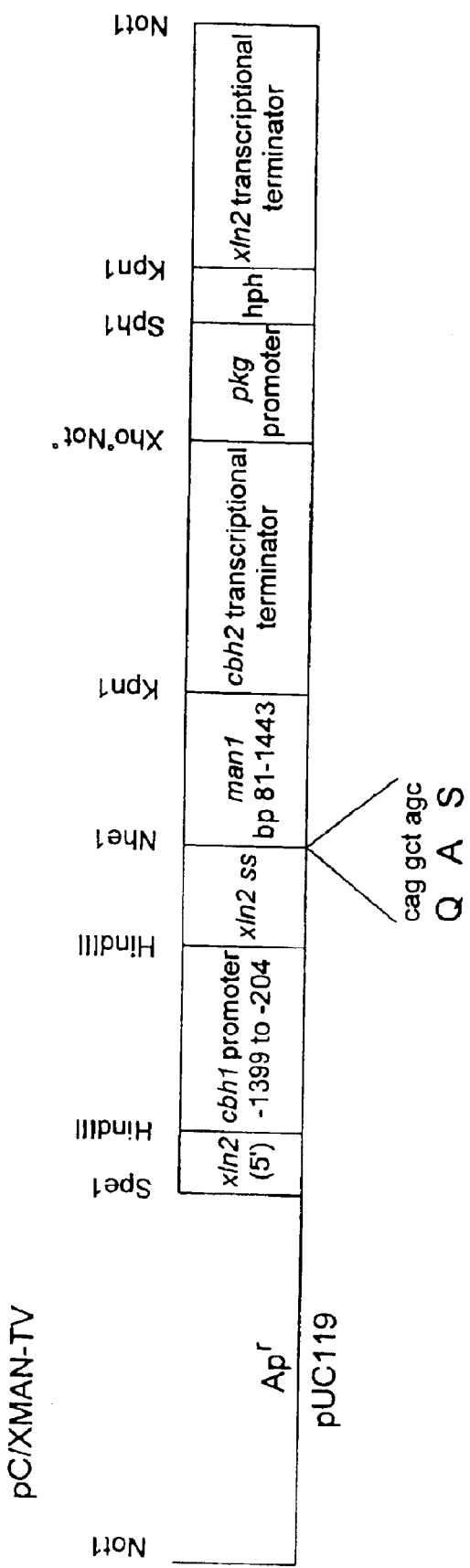
FIG. 7c shows the schematic of pC/XMAN-TV (FIG. 7c), both of which comprise the xln2 secretion signal. These latter two vectors are described in Example 28.
Figure 9A:
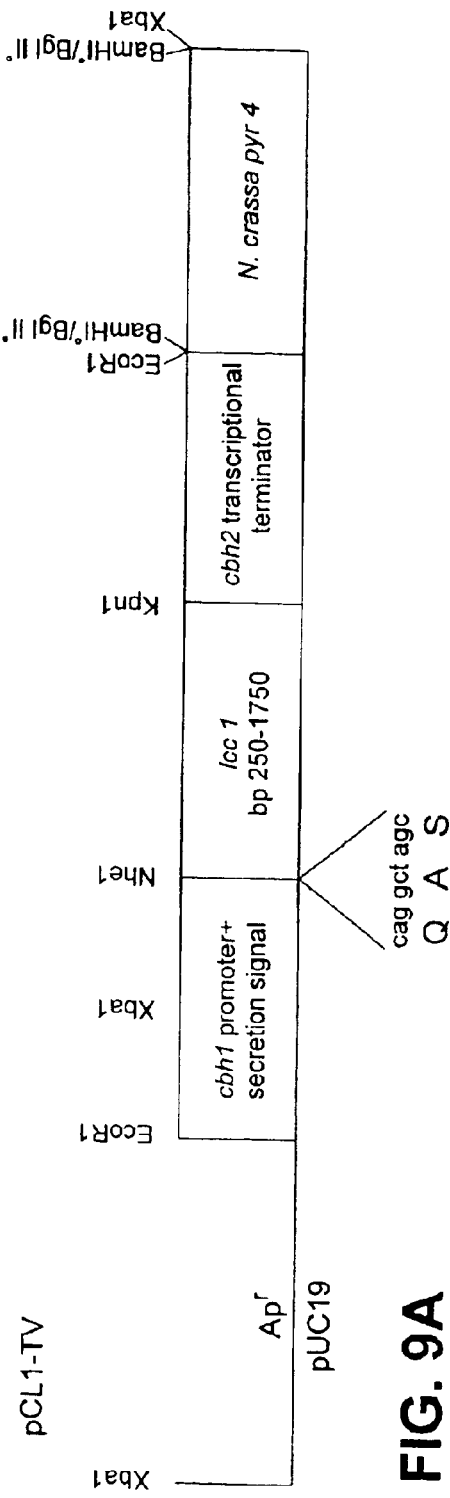
FIG. 9a shows pCL1-TV.
Figure 9B:
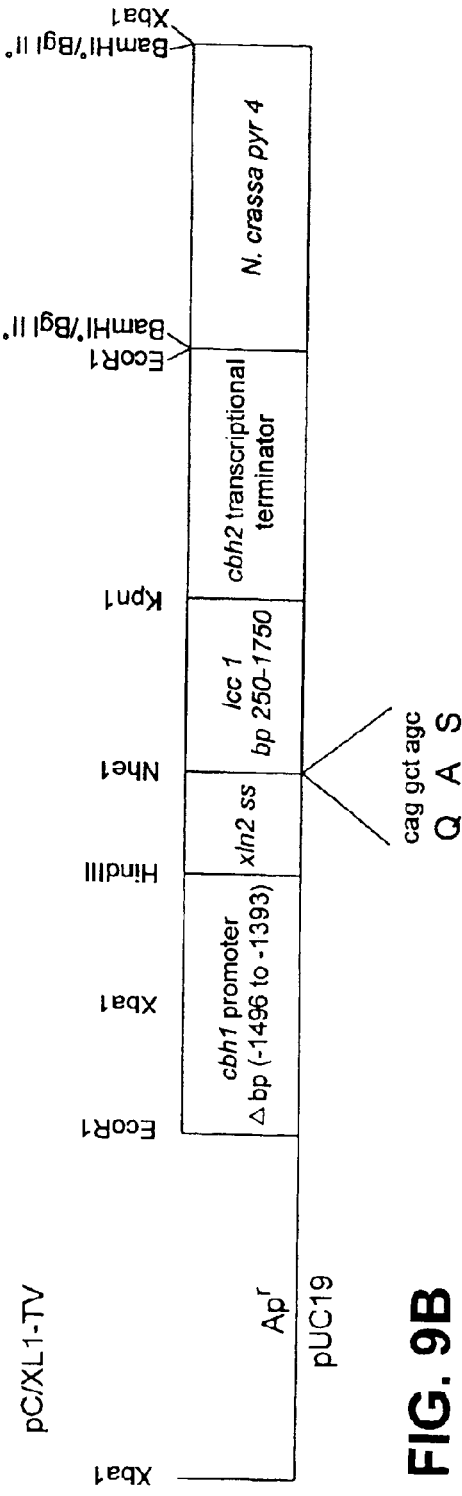
FIG. 9b shows pC/XL1-TV, comprising the xln2 secretion signal, as described in Example 32.
Figure 10:
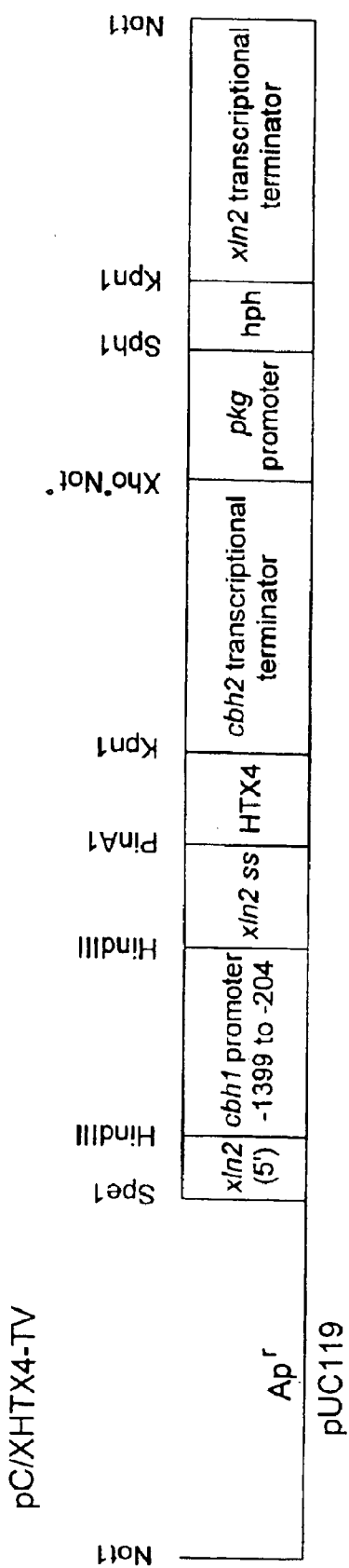
FIG. 10: Shows a schematic map of an expression vector comprising xylanase (pC/XHTX4-TV) as described in Example 34.

Genomic DNA was isolated from each strain as described in Example 1. For Southern blots, 1 μg of DNA was digested with 3–10 units of restriction endonuclease at 37° C. for at least 2 hours and the digestion products resolved on a 0.8% agarose gel in 0.04 M Tris-acetate, 1 mM EDTA. DNA was transferred by nylon membranes (Boehringer Mannheim) by capillary transfer (Sambrook et al., pp. 9.38–9.44). In FIGS. 4 and 5, lanes 2, 4, 6, 8, 10 and 12 contain digested M2C38 DNA and lanes 3, 5, 7, 9, 11 and 13 contain digested RutC30 DNA. The restriction endonucleases used were BamHI (lanes 2 and 3), EcoRI (lanes 4 and 5), XbaI (lanes 6 and 7), HindIII (lanes 8 and 9), SstI (lanes 10 and 11) and KpnI (lanes 12 and 13). In both figures, lane 1 contains λ-HindIII molecular size standards (Gibco/BRL, cat. no. 15612-013) and lane 14 contains 1 ng of unlabeled fragment used to make the probe. Southern blots were hybridized with a digoxigen-11-dUTP labelled random-primed probe prepared using the DIG Labeling and Detection Kit (Boehringer Mannheim). The template for the probe used in FIG. 4 was a 2.3 kb fragment comprising the *T. reesei* xln2 promoter and secretion signal (Saarelainen et al.). The template for the probe used in FIG. 5 was a 2.1 kb fragment comprising bp 574–2679 of the *T. reesei* bgl1 mature coding region (Barrett, et al.). After post-hybridization washes, dig-dUTP complexes were visualized by incubation with an anti-digoxigenin alkaline phosphatase conjugate (Boehringer Mannheim) followed by reaction with 5-bromo-4-chloro-3-indoyl phosphate and 4-nitro blue tetrazolium chloride (Boehringer Mannheim).

Example 9

Transformation of *T. reesei* RutC30, M2C38 and BTR48 via Microprojectile Bombardment The Biolistic PDS-1000/He system (BioRad; E.I. DuPont de Nemours and Company) was used to transform spores of *T. reesei* strains RutC30, M2C38 and BTR48, and all procedures were performed as recommended by the manufacturer. M-10 tungsten particles (median diameter of 0.7 μm) were used as nicrocarriers. The following parameters were used in the optimization of the transformation: a rupture pressure of 1100 psi, a helium pressure of 29 mm Hg, a gap distance of 0.95 cm, a macrocarrier travel distance of 16 mm, and a target distance of 9 cm. Plates were prepared with $1 \times 10^6$ spores on Potato Dextrose Agar media (PDA). Bombarded plates were incubated at 28° C. Four hours postbombardment, spores are subjected to primary selection by the overlaying of selective PDA media supplemented with 80 units/ml of HygB. The bombardment plates are incubated at 28° C. Transformants can be observed after 3–6 days growth; however, further incubation is necessary to achieve sporulation.

After sporulation has occurred, a secondary selection process is performed to isolate individual transformants. Spores are collected from the plate with an inoculating loop and resuspended in sterile water. This suspension is then filtered through a sterile syringe plugged with glass microfibers. This allows the passage of spores while retaining unwanted mycelia. A determination of the concentration of spores in this suspension is required and subsequent dilutions are plated onto PDA plates supplemented with 0.75%

Oxgall (Difco) and HygB (40 units/mL) to obtain 20–50 spores per plate. The Oxgall acts as a colony restrictor, thereby allowing the isolation of individual colonies on these secondary selection plates. Isolated colonies can be observed after 2–3 days.

Example 10
Southern Blot Analysis of Genomic DNA Isolated from *T. reesei* Strains RutC30, RC300, RC-302, M2C38, RM4-300, R4-301, RM4-302, BTR48, and RB4-301

Genomic DNA was isolated from each strain as described in Example 1. For Southern blots, 1 μg of DNA was digested with 3–10 units of Kpnl or XbaI at 37° C. for at least 2 hours and the digestion products resolved on a 0.8% agarose gel in 0.04 M Tris-acetate, 1 mM EDTA. DNA was transferred by nylon membranes (Boehringer Mannheim) by capillary transfer (Sambrook et al., pp. 9.38–9.44). Southern blots were hybridized with a digoxigen-11-dUTP labelled randomprimed probe prepared using the DIG Labeling and Detection Kit (Boehringer Mannheim). The template was a 1.3 kb EcoRI-Bgl II fragment comprising bp 1215–2464 of the published bgl1 sequence (Barrett et al.). After posthybridization washes, dig-dUTP complexes were visualized by incubation with an anti-digoxigenin alkaline phosphatase conjugate (Boehringer Mannheim) followed by reaction with the chemiluminescent reagent CSPD (Boehringer Mannheim) and exposure to X-ray film (Kodak). The results are summarized in Table 1.

| Component | g/L |
|---|---|
| Carbon sources** | 5–10 |
| Trace elements* | 1 mL/L |

*Trace elements solution contains 5 g/l $FeSO_4\text{-}7H_2O$; 1.6 g/l $MnSO_4\text{-}H_2O$; 1.4 g/l $ZnSO_4\text{-}7H_2O$.
**5 g/l glucose plus 10 g/l Solka floc (when the cbh1 or other cellulase promoter is used), 10 g/l xylan (when the xln2 promoter is used) or other carbon source compatible with the promoter directing the expression of the β-glucosidase. The carbon source can be sterilized separately as an aqueous solution at pH 2 to 7 and added to the remaining media.

The liquid volume per 1-liter flask is 150 mL, the initial pH is 5.5 and each flask is sterilized by steam autoclave for 30 minutes at 121° C. prior to inoculation.

For both untransformed (i.e., native) and transformed cells, spores are isolated from the PDA plates as described in Example 9 and $1-2 \times 10^6$ spores are used to inoculate each flask. The flasks are shaken at 200 rpm at a temperature of 28° C. for a period of 6 days. The filtrate containing the secreted protein was collected by filtration through GF/A glass microfibre filters (Whatman). The protein concentration was determined using the Bio-Rad Protein Assay (Cat. No. 500-0001) using *Trichoderma* cellulase as a standard. β-glucosidase activity is determined as described in Example 16.

Transformants were screened for the ability to produce at least 10-fold more β-glucosidase (in IU/mg) than the

TABLE 1 bgl1 copy number in parental and recombinant *T. reesei* strains

| Strain | Host | Promoter | Secretion signal | Vector | native bgl1 gene | # bgl1 vectors | total # bgl1 genes |
|---|---|---|---|---|---|---|---|
| RUTC30 | Same | bgl1 | bgl1 | none | Present | 0 | 1 |
| RC-300 | RutC30 | cbh1 | cbh1 | pCBG1-TV | Present | 1 | 2 |
| RC-302 | RutC30 | cbh1 | xln2 | pC/XBG1-TV | Absent | 1 | 1 |
| M2C38 | Same | bgl1 | bgl1 | None | Present | 0 | 1 |
| RM4-300 | M2C38 | cbh1 | cbh1 | pCBG1-TV | Absent | 2 | 2 |
| RM4-301 | M2C38 | xln2 | xln2 | pXBG1-TV | Present | 2 | 3 |
| RM4-302 | M2C38 | cbh1 | xln2 | pC/XBG1-TV | Present | 2 | 3 |
| BTR48 | Same | bgl1 | bgl1 | None | Present | 0 | 1 |
| RB4-301 | BRT48 | xln2 | xln2 | pXBG1-TV | Absent | 2 | 2 |

Example 11
Production of β-glucosidase in Liquid Cultures

This Example describes the methods used to determine the amount of β-glucosidase enzyme produced by a *Trichoderma* strain.

Individual colonies of *Trichoderma* are transferred to PDA plates for the propagation of each culture. Sporulation is necessary for the uniform inoculation of shake flasks which are used in testing the ability of the culture to produce the β-glucosidase and cellulase. The culture media is composed of the following:

| Component | g/L |
|---|---|
| $(NH_4)_2SO_4$ | 6.35 |
| $KH_2PO_4$ | 4.00 |
| $MgSO_4\text{-}7H_2O$ | 2.02 |
| $CaCl_2\text{-}2H_2O$ | 0.53 |
| CSL (corn steep liquor) | 6.25 |
| $CaCO_3$ | 10.00 | untransformed host strain as determined by the IU/ml of β-glucosidase activity of the culture filtrate divided by the protein concentration (in mg/ml) of the culture filtrate.

Example 12
Production of β-glucosidase by *T. reesei* Strains RutC30, RC-300, and RC-302 using Solka floc Carbon Source Based on previous successes using the cbh1 promoter and secretion signal to overexpress proteins in *Trichoderma*, the mature β-glucosidase coding region was placed downstream of the cbh1 promoter and secretion signal in the genetic construct shown in FIG. 1 and described in Example 5 (pCBG1-TV). The vector was introduced into *T. reesei* RutC30 by particle bombardment (Example 9) and the resulting transformant RC-300, produced 7 times more β-glucosidase activity than the parental strain (Table 2). This 7-fold increase resulted from the incorporation of one copy of the transformation vector into the host chromosomes (Example 10, Table 1). The larger increase in β-glucosidase activity obtained from one copy of a construct in which β-glucosidase is expressed using the cbh1 promoter and secretion signal suggests that this strategy is better than that employed by Barnett et al. and Fowler et al. which resulted in only a 5-fold increase in β-glucosidase activity from 10–15 copies of a construct in which β-glucosidase is expressed from its own promoter and secretion signal. However, the resulting 7-fold increase in β-glucosidase activity was still not sufficient to alleviate the shortage of β-glucosidase for cellulose hydrolysis.

The untransformed *T. reesei* strain RutC30 was transformed by particle bombardment (Example 9) with a genetic construct from the vector pC/XBG(XbaI)-TV encoding the mature *T. reesei* β-glucosidase enzyme linked to the *T. reesei* xylanase II secretion signal.

The untransformed strain RutC30 and the resulting transformed strain from this host, RC-302, were cultured using the procedures of Example 11 with 10 g/L Solka floc and 5 g/L glucose as carbon sources. The results are shown in Table 2.

The untransformed strain produced 0.14 IU of β-glucosidase per mg protein.

The transformant RC-302 with the CBH1 promoter and xylanase II secretion signal produced 19 IU/mg of β-glucosidase. This represents about a 136-fold improvement over the untransformed strain, which is very significant for a cellulose-to-ethanol process.

The transformant RC-302 with the CBH1 promoter and xylanase II secretion signal produced about 19 times more β-glucosidase activity than the best RC300 transformant with the CBH1 promoter and CBH1 secretion signal.

TABLE 2

Production of β-glucosidase in *T. reesei* strains RutC30, RC-300, and RC-302 in 150 ml flask cultures

| Strain | promoter | Secretion signal | β-g (IU/mg) |
|---|---|---|---|
| RutC30 | bgl1 | bgl1 | 0.14 |
| RC-300 | cbh1 | cbh1 | 1 |
| RC-302 | cbh1 | xln2 | 19 |

Example 13
Production of β-glucosidase by Strains M2C38 and RM4–302 using Solka floc Carbon Source.

The vector pCBG1-TV, in which the β-glucosidase is expressed from the CBH1 promoter and secretion signal (FIG. 1 and Example 5), was introduced into *T. reesei* M2C38 by particle bombardment (Example 9). The resulting transformant RM4-300 produced about 7–12 times more β-glucosidase activity than the parental strain (Table 3).

The untransformed *T. reesei* strain M2C38 was transformed by particle bombardment (Example 9) with a genetic construct from the vector pC/XBG(XbaI)-TV encoding the mature *T. reesei* β-glucosidase enzyme linked to *T. reesei* xylanase II secretion signal.

The untransformed strain M2C38 and the transformed strain from this host, RM4-302, were cultured using the procedures of Example 11 with 10 g/L Solka floc and 5 g/L glucose as carbon sources. The results are shown in Table 3.

The untransformed strain produced 0.35 IU of β-glucosidase per mg protein.

The transformant RM4-302 with the CBH1 promoter and xylanase II secretion signal produced 14.1 IU/mg of β-glucosidase. This represents about a 40-fold improvement over the untransformed strain, which is very significant for a cellulose-to-ethanol process.

The transformant RM4-302 with the CBH1 promoter and xylanase II secretion signal produced about 3 times more β-glucosidase activity than the transformant with the CBH1 promoter and CBH1 secretion signal. This is a significant difference, as the CBH1 promoter and secretion signal did not lead to sufficient production of β-glucosidase to completely suppress cellobiose production in hydrolysis.

TABLE 3

Production of β-glucosidase in *T. reesei* strains M2C38, RM4-300, and RM4-302 in 150 ml flask cultures

| Strain | promoter | Secretion signal | β-g (IU/mg) |
|---|---|---|---|
| M2C38 | bgl1 | bgl1 | 0.35 |
| RM4-300 | cbh1 | cbh1 | 4.5 |
| RM4-302 | cbh1 | xln2 | 14.1 |

Example 14
Production of β-glucosidase by *T. reesei* Strains M2C38 and RM4–301 using Xylan Carbon Source.

The untransformed *T. reesei* Strain M2C38 was transformed by particle bombardment (Example 9) with a genetic construct from the vector pXBG1-TV encoding the mature *T. reesei* β-glucosidase linked to the xylanase promoter and secretion signal.

The untransformed strain M2C38 and a transformed strain from this host, RM4-301, were cultured using the procedures of Example 11 with 5 g/L glucose and 10 g/L xylan as the carbon source. The results are shown in Table 4.

The untransformed strain produced 0.16 IU of β-glucosidase per mg protein. The transformant RM4-301 with the xylanase II promoter and xylanase II secretion signal produced 20.4 IU/mg of β-glucosidase. This represents about a 127-fold improvement over the untransformed strain, which is very significant for a cellulose-to-ethanol process.

TABLE 4

Production of β-glucosidase in *T. reesei* strains M2C38 and RM4-301 with xylan in 150 ml flask cultures

| Strain | promoter | Secretion signal | β-g (IU/mg) |
|---|---|---|---|
| M2C38 | bgl1 | bgl1 | 0.16 |
| RM4-301 | xln2 | xln2 | 20.4 |

Example 15
Production of β-glucosidase by Strains BTR-48 and RB48-301 using Solka floc carbon source.

The untransformed *T. reesei* strain BTR48 was transformed by particle bombardment with a genetic construct from the vector pXBG1-TV encoding the mature *T. reesei* β-glucosidase linked to the xylanase promoter and secretion signal.

The untransformed strain BTR48 and a transformed strain from this host, RB48-301, were cultured using the procedures of Example 11 with 5 g/L glucose and 10 g/L Solka floc as the carbon sources. The results are shown in Table 5.

The untransformed strain produced 0.16 IU of β-glucosidase per mg protein. The transformant RB48-301 with the xylanase II promoter and xylanase II secretion signal produced about 21.9 IU/mg of β-glucosidase. This represents about a 136-fold improvement over the untransformed strain, which is very significant for a cellulose-to-ethanol process.

TABLE 5

Production of β-glucosidase in *T. reesei* strains BTR48 and RB48-301 with Solka floc in 150 ml flask cultures

| Strain | promoter | Secretion signal | β-g (IU/mg) |
|---|---|---|---|
| BTR48 | bgl1 | bgl1 | 0.16 |
| RB48 | xln2 | xln2 | 21.9 |

Example 16
Measurement of β-glucosidase Activity of an Enzyme Mixture

The β-glucosidase activity of an enzyme is measured using the procedures of Ghose, "Measurement of Cellulase Activities," Pure and Appl. Chem., 59:257–268 (1987), as follows. The sample of enzyme is diluted to several concentrations in 50 mM sodium citrate buffer, pH 4.8, to a volume of 0.5 ml. A convenient range of dilutions is 3 to 24 times the estimated activity of the sample. For example, a 10 unit/ml sample should be diluted 1:30 to 1:240. Regardless of the dilutions used, a sample of 0.5 ml of the citrate buffer is added to each enzyme tube. The substrate is prepared as 15 mM (5.13 g/L) cellobiose. The dilute enzyme stocks and the substrate are separately preheated to 50° C. for 5 minutes, then a 0.5 ml aliquot of the substrate is added to each tube with enzyme. The test tubes are incubated for 30 minutes at 50° C. The reaction is terminated by immersing each tube in a boiling water bath for 5 minutes. The tubes are then vortex mixed, and the amount of sugar produced by each sample of enzyme is measured on a YSI glucose analyzer, taking into account the small background from the enzyme.

A unit of β-glucosidase activity is defined as the number of micromoles of glucose produced per minute. The activity is calculated based on Equation 1 using the average value from each of the dilutions which produces 0.15 to 1.5 mg/ml of glucose.

$$A = C*G*D \tag{1}$$

where A = activity, β-glucosidase units/ml (or micromoles glucose/ml/min)
C = 16.7 micromoles/mg/min
G = glucose produced, mg/ml
D = enzyme dilution, dimensionless

Example 17
Cellulose Hydrolysis

The purpose of this experiment was to demonstrate the effectiveness of the β-glucosidase made by the transformed *Trichoderma* in enhancing the hydrolysis of cellulose.

The enzymes used for this study were Iogen Cellulase, a commercial cellulase enzyme of Iogen Corporation, and the product of RM4-302 grown in a 30-liter fermentation vessel using the procedures described in Example 11, with twice the media concentration levels listed in that Example. The enzyme concentration was increased by ultrafiltration across an Amicon 10,000 MWCO membrane and normalized to the same cellulase activity as Iogen Cellulase. The activities of these two enzymes are shown in Table 6.

TABLE 6

Enzyme activities used in cellulose hydrolysis study

| Enzyme | B-glucosidase IU/ml | Cellulase FPU/ml | BG IU/mg @ 10 FPU/g |
|---|---|---|---|
| Iogen Cellulase | 112 | 140 | 8 |
| RM4-301 | 1170 | 140 | 83.6 |

The cellulose used for this study was pretreated oat hulls, prepared as per the procedures of Example 6 in Foody, et al, Improved Pretreatment Process for Conversion of Cellulose to Fuel Ethanol, U.S. Pat. No. 5,916,780.

Samples of pretreated oat hull cellulose of 0.5 grams were added to 25 ml flasks with 49.5 grams of 0.05 molar sodium citrate buffer, pH 4.8.

The enzymes were added to the flask in an amount corresponding to 10 FPU per gram of cellulose. The resulting β-glucosidase dosages are listed in Table 6.

In both cases, the flasks were shaken at 250 rpm and maintained at 50° C. for 24 hours. At this time, samples were taken, filtered to remove insoluble cellulose, and analyzed for glucose and cellobiose concentration using standard Dionex pulsed-amperometric HPLC carbohydrate analysis methods. The results are listed in Table 7.

Iogen Cellulase, the conventional *Trichoderma* cellulase, converted only 45% of the cellulose to glucose. This is unacceptably low for an ethanol process. The accumulation of cellobiose was significant, representing 13% of the cellulose.

The cellulase with enhanced β-glucosidase performed much better. The cellulose conversion to glucose reached 84%. The reason for this excellent performance was that cellobiose accumulation was negligible, due to the abundance of β-glucosidase.

TABLE 7

Hydrolysis of cellulose enhanced by high β-glucosidase

| Enzyme | Glucose (% of cellulose) | Cellobiose (% of cellulose) |
|---|---|---|
| Iogen Cellulase | 45 | 13 |
| RM4-301 | 84 | <1 |

Example 18
Comparison of the *Trichoderma reesei* xln2 and bgl1 Genes in Strains RutC30 and M2C38

Southern Blot analysis was performed on M2C38 and RutC30 DNA digested with six different restriction enzymes that cut both within and outside of the regions that encode the mature β-glucosidase and the xylanase secretion signal (Example 8) to determine if any polymorphisms exist between the two strains. As shown in FIGS. 4 and 5, the identical bands were found to hybridize with labelled probes prepared from M2C38 fragments encoding the mature β-glucosidase enzyme and the xylanase II promoter plus secretion signal, indicating no polymorphisms and a high degree of DNA sequence homology in these regions between the two strains.

The probes and primers used to identify and clone the M2C38 DNA sequences necessary to make the genetic constructs described in Examples 5–7 were based on published DNA sequences of the various genes from several different *Trichoderma reesei* strains including QM9414 (pgk, Vanhanen et al., 1989 and cbh2, Chen et al.), the QM9414 derivatives VTT-D79125 (xln2, Saarelainen et al.) and L27 (cbh1, Shoemaker et al.), and the strain RL-P37 derivative strain P40 (bgl1, Barnett et al.). All of these strains, like M2C38, are derived from strain QM6a (Carter, Allison, Rey and Dunn-Coleman, "Chromosomal and genetic analysis of the electrophoretic karyotype of *Trichoderma reesei*: mapping of the cellulase and xylanase genes," Molecular Microbiology 6: 2167–2174, 1992).

Because RutC30 is the QM6a-derived progenitor of M2C38, the inventors are confident that the method as described in Examples 24, for the isolation of the gene sequences used to make the β-glucosidase expression vectors described in Examples 5–7, will work equally well for the isolation of the same gene sequences from both M2C38 and RutC30. Based on the strain lineage described above and the Southern blot data, the inventors also have a high degree of confidence that genetic constructs prepared from RutC30 DNA will contain the identical DNA segments encoding the mature β-glucosidase enzyme and the xylanase II secretion signal as those prepared from M2C38 DNA. Since the constructs prepared from M2C38 DNA (Examples 5–7) result in enhanced β-glucosidase expression in both M2C38 and RutC30 (Examples 12–14), the inventors are also confident that genetic constructs made from RutC30 DNA will result in similar levels of enhancement of β-glucosidase activity in both RutC30 and M2C38.

Examples 19–33

Examples 19–33 outline the cloning and expression of several heterologous genes of interest within *T. reesei* using a xylanase secretion signal.

Example 19 describes the isolation of pyr4 auxotrophs of *Trichoderma reesei* strains M2C38 and BTR213. Examples 20 and 21 describe the transformation and expression of target enzymes (both endogenous and heterologous) by genetic constructs in *Trichoderma reesei* strains M2C38 and BTR213. Examples 22, 26 and 32 describe the cloning of the *T. reesei* eg2, and man1 genes, respectively.

Examples 23, 27, 28, 30 and 32 describe the construction of several genetic constructs for the expression of target enzymes in *Trichoderma reesei*. Examples 25, 29, 31 and 33 describe the transformation and expression of genetic constructs in *T. reesei* strains M2C38 and BTR213.

Example 19
Selection of M2C38 and BTR213 pyr4 Auxotrophs

The pyr4 gene encodes orotidine-5'-monophosphate decarboxylase, an enzyme required for uridine biosynthesis. Mutations in this gene render the cell incapable of growing in the absence of uridine. Mutations in this gene can be selected in the presence of the toxic inhibitor 5-fluoroorotic acid (FOA). FOA is an analogue of the pyrimidine precursor orotic acid. It is incorporated into wildtype *T. reesei* cells, thereby poisoning cells that are capable of uridine biosynthesis. Cells which contain a defective pyr4 gene are resistant to FOA but require uridine for growth.

To select for these mutants, *Trichoderma reesei* spores are plated on solid minimal media containing 1.2 mg/mL FOA, 2 mg/mL of uridine. The minimal media consisted of the following: 10 g/L of glucose; 10 g/L $KH_2PO_4$; 6 g/L $(NH_4)_2SO_4$; 1 g/L $MgSO_4\text{-}7H_2O$; 3 g/L tri-sodium citrate-$2H_2O$; 5 mg/L $FeSO_4\text{-}7H_2O$; 1.6 mg/L $MnSO_4\text{-}H2O$; 1.4 mg/L $ZnSO_4\text{-}7H_2O$; 2 mg/mL $CaCl_2\text{-}2H_2O$; pH 5.5. Spontaneous FOA resistant colonies appear within 3–4 days. Further selection identified mutants that required uridine for growth. Identification of mutants which specifically contained a defective pyr4 gene were identified by transformation with plasmid pNCP4hph containing a hygromycin resistance gene and the *Neurospora crassa* pyr4 gene. This vector was constructed by isolating the 3.2 kb BglII fragment from pFB6 (Buxton, F. P. and Radford, A., 1983, "Cloning of the structural gene for orotidine-5'-phosphate carboxylase of *Neurospora crassa* by expression in *Escherichia coli*. Mol. Gen. Genet. 190: 403–405) and cloning it into the unique BamHI site of pHPT136 (Example 5 above) to generate the vector pNCP4hph. Spores were transformed with pNCP4hph using microprojectile bombardment and selected on potato dextrose agar media containing hygromycin. Subsequent growth of hygromycin-resistant transformants on media lacking uridine identified those in which the defective pyr4 gene was complemented by the *N. crassa* pyr4 gene.

Example 20
Transformation of *Trichoderma reesei* by Particle Bombardment

The Biolistic PDS-1000/He system (BioRad; E.I. DuPont de Nemours and Company) was used to transform spores of *T. reesei* strains M2C38, BTR213 or the pyr4 auxotrophs of these strains and all procedures were performed as recommended by the manufacturer. M-10 tungsten particles (median diameter of 0.7 µm) were used as microcarriers. The following parameters were used in the optimization of the trans-formation: a rupture pressure of 1100 psi, a helium pressure of 29 mm Hg, a gap distance of 0.95 cm, a macrocarrier travel distance of 16 mm, and a target distance of 9 cm.

When transforming with vectors containing the *E. coli* hygromycin phosphotransferase (hph) gene as the selectable marker, plates were prepared with $1 \times 10^6$ spores on Potato Dextrose Agar media (PDA). Bombarded plates were incubated at 28° C. Four hours post-bombardment, spores are subjected to primary selection by the overlaying of selective PDA media supplemented with 80 units/ml of HygB. The bombardment plates are incubated at 28° C. After 3–6 days growth, individual transfornants are picked with a sterile toothpick, placed on individual PDA plates containing 40 units/ml HygB and incubated at 28° C. for 3–6 days.

When transforming with vectors containing the *N. crassa* pyr4 gene as the selectable marker, plates were prepared with $1 \times 10^6$ spores on minimal media (Example 19). Bombarded plates were incubated at 28° C. After 3–6 days growth, individual transformants are picked with a sterile toothpick, placed on a individual minimal media plates and incubated at 28° C. for 3–6 days.

Example 21
Production of Target Enzymes in Liquid Cultures

Individual colonies of native and transformed *Trichoderma* strains are transferred to PDA plates for the propagation of each culture. Sporulation is necessary for the uniform inoculation of shake flasks which are used in testing the ability of the culture to produce the target enzyme. The culture media is composed of the following:

| Component | g/L |
|---|---|
| $(NH_4)_2SO_4$ | 6.35 |
| $KH_2PO_4$ | 4.00 |
| $MgSO_4\text{-}7H_2O$ | 2.02 |
| $CaCl_2\text{-}2H_2O$ | 0.53 |
| CSL | 6.25 |
| $CaCO_3$ | 10.00 |

-continued

| Component | g/L |
|---|---|
| Trace elements* | 1 ml/L |
| Carbon sources** | 5–10 |

*Trace elements solution contains 5 g/l $FeSO_4*7H_2O$; 1.6 g/l $MnSO_4*H_2O$; 1.4 g/l $ZnSO_4*7H_2O$.
**5 g/l glucose plus 10 g/l Solka floc (when the cbh1 or other cellulase promoter is used), 10 g/l xylan (when the xln2 promoter is used) or other carbon source compatible with the promoter directing the expression of the β-glucosidase. The carbon source can be sterilized separately as an aqueous solution at pH 2 to 7 and added to the remaining media.

The liquid volume per 1-liter flask is 150 ml, the initial pH is 5.5 and each flask is sterilized by steam autoclave for 30 minutes at 121° C. prior to inoculation.

For both native and transformed cells, spores are collected from the plate with an inoculating loop and resuspended in sterile water. This suspension is then filtered through a sterile syringe plugged with glass microfibers. This allows the passage of spores while retaining unwanted mycelia. After determination of the concentration of spores in this suspension, $1-2 \times 10^6$ spores are used to inoculate each flask. The flasks are shaken at 200 rpm at a temperature of 28° C. for a period of 6 days. The filtrate containing the secreted protein was collected by filtration through GF/A glass microfibre filters (Whatman). The protein concentration is determined using the Bio-Rad Protein Assay (Cat. No. 500-0001) using *Trichoderma* cellulase as a standard.

Example 22
Cloning of the *T. reesei* Endoglucanase II Gene (eg2) from Strain M2C28

Genomic clones containing the *T. reesei* eg2 5' untranslated, structural and 3' untranslated regions were isolated from a *Trichoderma* M2C38 DNA genomic λDASH library using methods previously described (Examples 2 and 4 above). A digoxigenin-11-dUTP labelled eg2 gene probe was prepared from M2C38 genomic DNA using Pwo polymerase and primers designed to amplify bp 262–1692 of the published DNA sequence (Saloheimo, Lehtovaara, Penttila, Teeri, Stahlberg, Johansson, Petterson, Claeyssens, Tomme and Knowles, 1988, "EGIII, a new endoglucanase from *Trichoderma reesei*: the characterization of both gene and enzyme", Gene 63: 11–21 herein referred to as Saloheimo et al.) and subsequently used as a probe to screen the λDASH library. A 6.0 kb EcoRI fragment from one of the positively hybridizing clones was isolated and subcloned into the EcoRI site of pUC119 to generate the subclone pEG2gen.

Example 23
Construction of Endoglucanase II Overexpression Vectors pEG2-TV and pC/X/REG2-TV This example describes the construction of vectors expressing the mature endoglucanase II coding region under the control of the *T. reesei* cbh1 promoter and the eg2 or xln2 secretion signal.

Using the eg2 subclone pEG2gen as a template, the DNA sequence encoding the endoglucanase II protein with its own secretion signal (bp 262–1692) was amplified with Pwo polymerase (Boehringer) and primers designed to introduce an SphI site at bp 260–265 and a KpnI site directly downstream of the stop codon at bp 1692. The resulting PCR product was inserted as a blunt-ended fragment into the SmaI site of pUC119 to make the plasmid pEG2-6 and the sequence verified. Before an expression cassette from which this eg2 gene could be expressed from the cbh1 promoter could be made, a 2.2 kb fragment containing the cbh1 promoter was amplified from the cbh1 genomic subclone pCB 152 (Example 3, above) using Pwo polymerase, a primer that anneals upstream of the EcoRI site of the pUC119 polylinker and a reverse primer designed to introduce an SphI site at the start codon of cbh1 (bp 209–214 of the published cbh1 sequence, Shoemaker, Schweikart, Ladner, Gelfand, Kwok, Myambo and Innis, "Molecular cloning of exo-cellobiohydrolyase I derived from *Trichoderma reesei* strain L27", Biotechnology 1: 691–696, 1983 hereafter referred to as Shoemaker et al.). This amplified fragment was digested with EcoRI and SphI and inserted into pBR322L (Example 5, above), a derivative of pBR322 into which a synthetic SphI-NotI-SalI linker was inserted between the existing SphI and SalI sites of pBR322 to generate the plasmid pBRC1pro. The eg2 gene was isolated as a 1.4 kb SphI/KpnI fragment from pEG2-6 and inserted between the unique SphI and KpnI sites upstream of the cbh2 transcriptional terminator in the plasmid pCB219N (Example 5, above). A 3.3 kb fragment comprising the eg2 gene and cbh2 transcriptional terminator was subsequently isolated by SphI/NotI digestion and inserted between the SphI and NotI sites directly downstream of the cbh1 promoter in pBRC1pro. The resulting expression cassette plasmid, pCEG2, contains the eg2 gene (encoding the mature secreted edoglucanase II enzyme and its own secretion signal) linked to the cbh1 promoter and cbh2 terminator sequences. This plasmid was further modified to insert a unique XhoI site at the 3' end of the cbh2 terminator by digestion at the unique NotI site, blunting with Klenow and the addition of XhoI linkers (Cat. No. 1073, New England Biolabs) to make a new expression cassette plasmid pEG2-Xho. To make the final transformation vector, pEG2-TV (FIG. 6a), pCEG2-Xho was digested at the unique XhoI site at the 3' end of the cbh2 terminator and then digested at the unique XbaI site at bp -1392 in the cbh1 promoter in order to isolate the 5.6 kb expression cassette containing the eg2 gene under the control of the cbh1 promoter. This fragment was then inserted upstream of the hph selection cassette in pHPT136 (Example 5, above) which had been digested at the unique XhoI and XbaI site. Prior to transformation of *T. reesei* strain M2C38, the transformation vector pEG2-TV was digested with XbaI and NotI, the fragments separated by agarose gel electrophoresis and the larger band containing the eg2 construct purified.

To make an expression cassette from which the mature endoglucanase II enzyme is linked to the xln2 secretion signal under the control of the cbh1 promoter, bp 331–1692 of the published eg2 sequence (Saloheimo et al.) were amplified with Pwo polymerase and primers designed to introduce a unique NheI site directly upstream of bp 331 and a unique KpnI site directly downstream of bp 1692 using the genomic subclone pEG2gen as template. The resulting blunt-ended fragment was inserted into the SmaI site of pUC119 to generate the plasmid pE1 and the sequence of the eg2 gene verified. The 1.3 kb fragment encoding the mature endoglucanase II enzyme (without a secretion signal) was isolated from pE1 by NheI/KpnI digestion and inserted upstream of the cbh2 terminator in the plasmid pCB219N-HB to generate pCB219N-E1. pCB219N-HB is a derivative of pCB219N (Example 5, above) in which a synthetic a HindIII-SphI-NheI-BamHI linker was inserted between the existing HindIII and BamHI sites upstream of the cbh2 terminator fragment in of pCB219. A 3.2 kb fragment comprising the eg2 coding region and cbh2 terminator sequences were isolated by NheI/NotI digestion of pCB219N-E1 and inserted between the NheI and NotI sites directly downstream of the xln2 promoter and secretion signal in the plasmid pBR322LXN (Example 6, above) to generate pXE2. A 1.3 kb HindIII fragment comprising bp −1400 to −121 of the xln2 promoter in pXE2 was replaced by a modified 1.2 kb HindIII fragment comprising bp −1399 to −204 of the cbh1 promoter but with a new XbaI site at bp −1393 to −1388 which was prepared by PCR amplification using the cbh1 promoter-containing plasmid pBR322LCS as template. From the resulting plasmid pC/XRE2-Xba, a ~4.9 kb XbaI/NotI fragment comprising the modified cbh1 promoter, xln2 secretion signal, eg2 coding region and cbh2 terminator was isolated from pC/XRE2-Xba and used to replace the XbaI/NotI fragment in pCE2 comprising the cbh1 promoter and secretion signal, eg2 coding region and cbh2 terminator to generate the expression cassette plasmid pC/XRE2. Note that the XbaI site in the cbh1 promoter of pCE2 is the endogenous site located at bp −1497 to −1492. Therefore, in the expression cassette plasmid pC/XRE2, bp −1496 to −1393 of the cbh1 promoter are lost as a result of fusing the endogenous XbaI site of the native cbh1 promoter from pCE2 with the engineered XbaI site of the modified cbh1 promoter in pC/XE2-Xba. To make the final transformation vector pC/XRE2-TV (FIG. 6b), the eg2 expression cassettes were isolated from pCE2 and pC/XRE2 by EcoRI digestion (which cuts at the 5' end of the cbh1 promoter and the 3' end of the cbh2 terminator). These fragments were then inserted into the unique EcoRI site of the N. crassa pyr4 selection cassette plasmid pNCBgl. pNCBgl was constructed by inserting the 3.2 kb BglII fragment comprising the promoter, coding region and terminator of the N. crassa pyr4 gene from pFB6 into the BamHI site in the polylinker of pUC19. The orientation of the insert was chosen such that the entire genetic construct comprising the eg2 expression cassette and the N. crassa pyr4 selection cassette could be isolated away from the pUC sequences by XbaI digest. Prior to transformation of T. reesei strain BTR213, the transformation vector pC/XRE2-TV were digested with XbaI, the fragments separated by agarose gel electrophoresis and the larger band containing the eg2 constructs purified.

Example 24

Southern Blot Analysis of Trichoderma Strains BTR213, 201-2A, 843-2 and 845-2

Genomic DNA was isolated from native and transformed Trichoderma strains as previously described (Example 1, above). For Southern blots, 1 µg of DNA was digested with 3–10 units of restriction enzyme at 37° C. for at least 2 hours and the digestion products resolved on a 0.8% agarose gel in 0.04 M Tris-acetate, 1 mM EDTA. DNA was transferred to nylon membranes (Boehringer Mannheim) by capillary transfer (Sambrook et al., pp. 9.38–9.44). Southern blots were hybridized with a digoxigen-11-dUTP labelled random-primed probe prepared using the DIG Labelling and Detection Kit (Boehringer Mannheim). The template was a 1.3 kb EcoRI-BglII fragment isolated from the plasmid pE1 (Example 22, above) and comprising bp 331–1692 of the published eg2 sequence (Saloheimo, et al.). After post-hybridization washes, dig-dUTP complexes were visualized by incubation with an anti-digoxigenin alkaline phosphatase conjugate (Boehringer Mannheim) followed by reaction with 5-bromo-4-chloro-3-indoyl phosphate and 4-nitro blue tetrazolium chloride. The results are summarized in Table 8.

TABLE 8 eg2 copy number in parental and recombinant T. reesei strains

| Strain | Host | Promoter | Secretion signal | Vector | # eg2 vectors | total # eg2 genes |
|---|---|---|---|---|---|---|
| BTR213 | same | eg2 | eg2 | none | 0 | 1 |
| 201-2A | BTR213 | cbh1 | eg2 | pE2-TV | 2 | 3 |
| 843-2 | BTR213 | cbh1 | xln2 | pC/XRE2-TV | 1 | 2 |
| 845-2 | BTR213 | cbh1 | xln2 | pC/XRE2-TV | 2 | 3 |

Example 25

Production of Endoglucanase II by Native and Transformed T. reesei Strains

T. reesei strain BTR213 or its pyr4 auxotroph was transformed by particle bombardment (Example 20) with genetic constructs from the vectors pE2-TV and pC/XRE2-TV encoding the endoglucanase II enzyme linked to the eg2 or xln2 secretion signal under the control of the cbh1 promoter. The native strain BTR213 and the resulting transformed strains were cultured using the procedures of Example 21 with 10 g/l solka floc and 5 g/l glucose as carbon source.

Measurement of the Endoglucanase Activity of an Enzyme Sample

Endoglucanase activity is determined by measuring the release of reducing sugars from a carboxymethyl cellulose (CMC) substrate. The sample of enzyme is diluted to several concentrations in 50 mM sodium citrate buffer, pH 4.8, to a volume of 0.5 ml. A convenient range of dilutions is 2–20 times the estimated activity of the sample. For example, a 1000 unit/ml sample should be diluted 1:2000 to 1:20,000. Regardless of the dilutions used, a sample of 0.5 ml of the citrate buffer is added to each enzyme tube. The substrate is prepared as 1% CMC in 50 mM citrate, pH 4.8. The dilute enzyme stocks and the substrate are separately preheated to 50° C. for 5 minutes, then a 0.5 ml aliquot of the substrate is added to each tube with enzyme. The test tubes are incubated for 30 minutes at 50° C. The reaction is terminated by the addition of 3 ml of DNS reagents (1% dinitrosalycilic acid, 1% sodium hydroxide, 0.2% phenol, 0.05% sodium metabisulfite in $H_2O$) and immersing each tube in a boiling water bath for 10 minutes. After boiling, 1 ml of an aqueous 40% sodium potassium tartrate solution is added to each tube. The tubes are then vortex mixed, cooled and the amount of soluble reducing sugars that were released from the substrate and that reacted with the DNS reagent determined by measuring the absorbance at 550 nm versus a standard curve generated from solutions containing 0.18–0.5 mg/ml glucose (a reducing sugar) in 50 mM citrate, pH 4.8. The activity of the culture is then calculated by comparing the ml of the culture filtrate required to produce of 0.5 mg/ml reducing sugar compared the ml of a control endoglucanase enzyme solution of known activity required to release 0.5 mg/ml reducing sugar under the same conditions.

The culture filtrates were collected as described in Example 21 and assayed for endoglucanase activity. The results are shown in Table 9.

TABLE 9

Production of endoglucanase in *T. reesei* strains BTR213, 201-2A, 843-2 and 845-2 in 150 ml flask cultures

| Strain | Vector | promoter | secretion signal | carbon source | CMC U/mg |
|---|---|---|---|---|---|
| BTR213 | none | eg2 | eg2 | solka floc | 9.9 |
| 201-2A | pE2-TV | cbh1 | eg2 | solka floc | 20 |
| 843-2 | pC/XRE2-TV | cbh1 | xln2 | solka floc | 35 |
| 845-2 | pC/XRE2-TV | cbh1 | xln2 | solka floc | 29 |

The untransformed strain produced 9.9 IU of endoglucanase per mg protein. The transformant 210-2A with 2 copies of the cbh1 promoter and eg2 secretion signal produced 2 times more endoglucanase or ~22 IU/mg while transformants 843-2 and 845-2 with the cbh1 promoter and the xln2 secretion signal produced 29–35 IU/mg which is 3.3 times more endoglucanase than the native strain or 1.3–1.6 times more than the transformant with the eg2 secretion signal Example 26
Cloning of the *T. reesei* M2C38 β-mannanase Gene This example describes the cloning of the *T. reesei* man1 gene from a genomic library Total RNA from *T. reesei* M2C38 was isolated and purified as follows: mycelia from cellulose-induced cultures were filtered through Whatman filter paper and washed with cold 50 mM Tris, 10 mM EDTA pH 8.0 buffer. The fungal cakes were frozen immediately in dry ice and powdered in a blender. Each gram of biomass was extracted for 10 min with 4 volumes of 4 M guanidium EDTA and 1% B-mercaptoethanol and centrifuged at 5000×g to pellet cell debris. Supernatants (3.5 ml) were layered onto a 1.5 ml cushion of 5.7 M CsCl-0.10M EDTA pH 7.0 and ultracentrifuged for 16 hours at 30,000 rpm in a Beckman SW50.1 swinging bucket rotor. RNA pellets were washed with 70% ethanol, dissolved in diethylpyrocarbonate-treated water (depc-$H_2O$), precipitated with 2.5 M ammonium acetate and 3 volumes of ethanol; the pellet was dissolved in depc-$H_2O$ and stored at −80° C. For first-strand cDNA synthesis, 60 µg of total RNA in 20 µl depc-$H_2O$ was pre-treated with 2 µl of 0.1 M methyl mercuric hydroxide for 10 min at room temperature. Samples were cooled on ice and neutralized with 4 µl of 0.7 M β-mercaptoethanol. The RNA was then precipitated with 3 vol of ethanol and the pellet dissolved in 20 µl depc-$H_2O$. First-strand synthesis was performed with AMV Reverse Transcriptase (Pharmacia) and oligo-dT primers following the manufacturer's protocols. A mannanase-specific probe was amplified from the first strand cDNA using primers specific for the 5' and 3' ends of the mannanase coding region (bp 88–1443 of the published man1 sequence, Stalbrand, Saloheimo, Vehmaanpera, Henrissat and Pentilla, 1995, "Cloning and Expression in *Saccharomyces cerevisiae* of a *Trichoderma reesei* β-mannanase gene containing a cellulose binding domain", Appl. Environ. Micro. 61: 1090–1097) with Taq polymerase and digoxigenin-11-dUTP (Boehringer). This probe was then used to screen the λDASH library prepared from BamHI-digested M2C38 genomic DNA as previously described (Examples 2 and 4, above). Positively hybridizing clones were selected and purified.

Example 27
Construction of Mannanase Overexpression Vector pCMAN-TV

This example describes the construction of a vector containing the *Trichoderma* cbh1 promoter and secretion signal and the mature mannanase coding region.

Using the man1 λDASH clone as a template, the DNA sequence encoding the secreted mannanase protein (bp 88–1443) was amplified with Pwo polymerase (Boehringer) and primers designed to introduce an NheI site at bp 88–93 and a KpnI site directly downstream of the stop codon at bp 1443. The resulting PCR product was inserted as a blunt-ended fragment into the SmaI site of pUCI 18 to make the plasmid pManGNK and the sequence verified. The man1 fragment was isolated from pManGNK by digestion with NheI and KpnI and inserted into the expression cassette plasmid pBR322LEC which had been digested with NheI and KpnI to make the expression cassette plasmid pLEC-MAN. pBR322LEC was constructed from pBR322LCS which contains the 2.3 kb fragment of the *T. reesei* cbh1 gene comprising the promoter and secretion signal sequences (Example 5, above) as follows: NheI linkers were ligated to pBR322LCS that had been linearized by SphI digestion and the ends made blunt with T4 DNA polymerase (Gibco/BRL); after digestion by NheI, the plasmid was recircularized with T4DNA ligase to make the plasmid pBR322LCN. A 1.9 kb NheI/NotI fragment containing the transcriptional terminator of the *T. reesei* cbh2 gene and a unique KpnI and NotI sites at the 5' and 3' ends of the terminator was isolated by NheI/NotI digestion of pCB219N-HB (Example 22, above) and inserted between the unique NheI and NotI sites in pBR322LCN to make pBR322LEC. To make the final transformation vector pCMAN-TV (FIG. 7a), pLECMAN was digested at the unique NotI site at the 3' end of the cbh2 terminator, blunted with Kienow, and then digested at the unique XbaI site at bp −1392 in the cbh1 promoter in order to isolate the 5.6 kb expression cassette containing the man1 gene under the control of the cbh1 promoter and secretion signal. This fragment was then inserted upstream of the hph selection cassette in pHPT136 (Example 5, above) which had been digested at the unique XhoI site, blunted with Klenow and then digested at the adjacent unique XbaI site. Prior to transformation of *T. reesei* strain M2C38, the transformation vector pCMAN-TV was digested with XbaI and NotI, the fragments separated by agarose gel electrophoresis and the larger band containing the man1 construct purified.

Example 28
Construction of the Mannanase Overexpression Vectors pXMAN-TX and pC XMAN-TV This example describes the construction of vectors expressing the mature mannanase coding region under the control of the *T. reesei* xln2 promoter and secretion signal or the *T. reesei* cbh1 promoter and xln2 secretion signal.

A 3.3 kb NheI/NotI fragment comprising the man1 coding region and cbh2 transcriptional terminator was isolated by NheI/NotI digestion of pBR322LEC (Example 27, above) and inserted downstream of the *T. reesei* xln2 promoter and secretion signal sequences contained in the plasmid pBR322SpXN (Example 6, above) to generate the expression cassette plasmid pXMAN. A 1.2 kb HindIII fragment comprising bp −1399 to −204 of the *T. reesei* cbh1 promoter isolated by HindIII digestion of pBR322LCS (Example 5, above) was used to replace a 1.3 kb HindIII fragment comprising bp −1400 to −121 of the xln2 promoter in pXMAN to generate the expression cassette plasmid pC/XMAN. To make the final transformation vectors pXMAN-TV (FIG. 7b) and pC/XMAN-TV (FIG. 7c), the expression cassette were isolated from pXMAN and pC/XMAN digestion at the unique NotI site at the 3' end of the cbh2 terminator, blunted with Klenow, and then digested at the unique XbaI site at bp −1392 in the cbh1 promoter in order to isolate the 5.6 kb expression cassettes containing the man1 gene under the control of the xln2 promoter and secretion signal or the cbh1 promoter and xln2 secretion signal. These fragments were then inserted upstream of the hph selection cassette in pHPTI36X (Example 6, above) which had been digested at the unique XhoI site, blunted with Klenow and then digested at the adjacent unique XbaI site. Prior to transformation of T. reesei strain M2C38, the transformation vectors pXMAN-TV and pC/XMAN-TV were linearized by digestion with NotI.

Example 29
Production of Mannanase by Native and Transformed T. reesei Strains

T. reesei strain M2C38 was transformed by particle bombardment (Example 20) with genetic constructs from the vectors pCMAN-TV and pC/XMAN-TV encoding the mature mannanase enzyme linked to the cbh1 or xln2 secretion signal under the control of the cbh1 promoter. The native strain M2C38 and the resulting transformed strains were cultured using the procedures of Example 21 with 10 g/l solka floc and 5 g/l glucose as carbon source.

Measurement of Mannanase Activity of an Enzyme Sample

Mannanase activity is determined by measuring the release of reducing sugars from a mannan substrate. The sample of enzyme is diluted to several concentrations in 50 mM sodium citrate buffer, pH 4.8 , to a volume of 0.5 ml. A convenient range of dilutions is 5–40 times the estimated activity of the sample. For example, a 10 unit/ml sample should be diluted 1:50 to 1:400. Regardless of the dilutions used, a sample of 0.5 ml of the citrate buffer is added to each enzyme tube. The substrate is prepared as 1% locust bean gum mannan in 50 mM citrate, pH 4.8. The dilute enzyme stocks and the substrate are separately preheated to 50° C. for 5 minutes, then a 0.5 ml aliquot of the substrate is added to each tube with enzyme. The test tubes are incubated for 30 minutes at 50° C. The reaction is terminated by the addition of 3 ml of DNS reagents (1% dinitrosalycilic acid, 1% sodium hydroxide, 0.2% phenol, 0.05% sodium metabisulfite in $H_2O$) and immersing each tube in a boiling water bath for 10 minutes. After boiling, 1 ml of an aqueous 40% sodium potassium tartrate solution is added to each tube. The tubes are then vortex mixed, cooled and the amount of soluble reducing sugars that were released from the substrate and that reacted with the DNS reagent determined by measuring the absorbance at 550 nm versus a standard curve generated from solutions containing 0.18–0.5 mg/ml glucose (a reducing sugar) in 50 mM citrate, pH 4.8. The activity of the culture is then calculated by comparing the ml of the culture filtrate required to produce of 0.5 mg/ml reducing sugar compared the ml of a control mannanase enzyme solution of known activity required to release 0.5 mg/ml reducing sugar under the same conditions.

The culture filtrates were collected as described in Example 21 and assayed for mannanase activity as described above. The results are shown in Table 10.

TABLE 10

Production of mannanase in T. reesei strains M2C38, 5D and 82D in 150 ml flask cultures

| Strain | Vector | promoter | secretion signal | carbon source | MU/mg |
|---|---|---|---|---|---|
| M2C38 | none | man1 | man1 | solka floc | 3.58 |
| 5D | pCMAN-TV | cbh1 | cbh1 | solka floc | 6.72 |
| 82D | pC/XMAN-TV | cbh1 | xln2 | solka floc | 16.22 |

The untransformed strain produced 3.58 IU of mannanase per mg protein. The transformant 5D with the cbh1 promoter and secretion signal produced 1.9 times more mannanase or 6.72 IU/mg while transformant 82D with the cbh1 promoter and the xln2 secretion signal produced 16.22 IU/mg which is 4.5 times more mannanase than the native strain or 2.4 times more than the transformant with the cbh1 secretion signal T. reesei strain M2C38 was transformed by particle bombardment (Example 20) with a genetic construct from the vector pXMAN-TV encoding the mature mannanase enzyme linked to the xln2 secretion signal under the control of the xln2 promoter. The native strain M2C38 and the resulting transformed strains were cultured using the procedures of Example 21 with 10 g/l xylan and 5 g/l glucose as carbon source.

The culture filtrates were collected as described in Example 21 and assayed for mannanase activity as described above. The results are shown in Table 11.

TABLE 11

Production of mannanase in T. reesei strains M2C38 and 17D in 150 ml flask cultures

| Strain | Vector | promoter | secretion signal | carbon source | MU/mg |
|---|---|---|---|---|---|
| M2C38 | none | man1 | man1 | xylan | 0.3 |
| 17D | pXMAN-TV | xln2 | xln2 | xylan | 2.81 |

The untransformed strain produced 0.3 IU of mannanase per mg protein when xylan is used as the carbon source. The transfomant 17D with the xln2 promoter and secretion signal produced 9.4 times more mannanase or 2.81 IU/mg.

Example 30

Construction of Humicola insolens endoglucanase 2 expression vectors pChHE2-TV and pC/XhHE2-TV This example describes the construction of vectors expressing the mature H. isolens endoglucanase II coding region under the control of the T. reesei cbh1 promoter and secretion signal or the T. reesei cbh1 promoter and xln2 secretion signal.

In order to clone the coding region of the mature endoglucanase H gene (cmc3), Humicola insolens genomic DNA was isolated from H. insolens strain ATCC22082 biomass grown in media containing 24 g/l Corn Steep Liquor, 24 g/L glucose and 0.5 g/l $CaCO_3$, pH 5.5 at 37° C. for 48 hours (as described in Barbesgaard, Jensen and Holm, 1984, "Detergent Cellulase, U.S. Pat. No. 4,435,307) using the methods previously described (Example 8). This H. insolens genomic DNA was then used as a template to amplify the coding region of the mature endoglucanase II enzyme with Pwo polymerase and primers designed to introduce a unique NheI site directly upstream of bp 64 and a unique KpnI site directly downstream of bp 1182 of the H. insolens cmc3 sequence (GenBank accession no. X76046). The amplified fragment was digested with NheI and KpnI and was used to replace the man1 gene in the expression cassette plasmid pCMAN (Example 26) that had been digested with NheI and KpnI. In the resulting cmc3 expression cassette plasmid, pChHE2, expression of the cmc3 sequence will be driven by the cbh1 promoter and secretion signal. In order to make the expression cassette in which the cmc3 gene is linked to the xln2 secretion signal, pC/XhHE2, the cmc3 PCR product which had been digested with NheI and KpnI was used to replace the eg2 gene in the expression cassette plasmid pCE2 (Example 22, above) that had been digested with NheI and KpnI.

To make the transformation vectors pChHE2-TV (FIG. 8a) and pC/XhHE2-TV (FIG. 8b), the cmc3 expression cassettes were isolated from pChHE2 and pC/XE2 by EcoRI digestion (which cuts at the 5' end of the cbh1 promoter and the 3' end of the cbh2 terminator). These fragments were then inserted into the unique EcoRI site of the *N. crassa* pyr4 selection cassette plasmid pNCBg1 (Example 23, above). The orientation of the insert was chosen such that the entire genetic construct comprising the cmc3 expression cassette and the *N. crassa* pyr4 selection cassette could be isolated away from the pUC sequences by XbaI digest. Prior to transformation of *T. reesei* strain M2C38, the transformation vectors pChHE2-TV and pC/XhHE2-TV were digested with XbaI, the fragments separated by agarose gel electrophoresis and the larger band containing the cmc3 constructs purified.

Example 31
Production of *H. insolens* Endoglucanase 2 by Native and Transformed *T. reesei* Strains

*T. reesei* strain M2C38 was transformed by particle bombardment (Example 20) with genetic constructs from the vectors pChHE2-TV and pC/X hHE2-TV encoding the mature *H. insolens* endoglucanase II enzyme linked to the cbh1 or xln2 secretion signal under the control of the cbh1 promoter. The native strain M2C38 and the resulting transformed strains were grown in 14-liter fermentation vessels using the procedures described in Example 21, with twice the media concentration levels listed in that Example.

Measurement of the High pH Endoglucanase Activity of an Enzyme Sample

High pH endoglucanase activity is determined by measuring the release of reducing sugars from a hydroxylethyl cellulose (HEC) substrate. The sample of enzyme is diluted to several concentrations in 50 mM phosphate buffer, pH 7.0, to a volume of 0.5 ml. A convenient range of dilutions is 2–20 times the estimated activity of the sample. For example, a 1000 unit/ml sample should be diluted 1:2000 to 1:20,000. Regardless of the dilutions used, a sample of 0.5 ml of the citrate buffer is added to each enzyme tube. The substrate is prepared as 3% HEC in 50 mM phosphate, pH 7.0. The dilute enzyme stocks and the substrate are separately preheated to 60° C. for 5 minutes, then a 0.5 ml aliquot of the substrate is added to each tube with enzyme. The test tubes are incubated for 30 minutes at 60° C. The reaction is terminated by the addition of 3 ml of DNS reagent (1% dinitrosalycilic acid, 1% sodium hydroxide, 0.2% phenol, 0.05% sodium metabisulfite in $H_2O$) and immersing each tube in a boiling water bath for 10 minutes. After boiling, 1 ml of an aqueous 40% sodium potassium tartrate solution is added to each tube. The tubes are then vortex mixed, cooled and the amount of soluble reducing sugars that were released from the substrate and that reacted with the DNS reagent determined by measuring the absorbance at 550 nm versus a standard curve generated from solutions containing 0.18–0.5 mg/ml glucose (a reducing sugar) in 50 mM phosphate, pH 7.0. The activity of the culture is then calculated by comparing the ml of the culture filtrate required to produce of 0.5 mg/ml reducing sugar compared the ml of a control high pH endoglucanase enzyme solution of known activity required to release 0.5 mg/ml reducing sugar under the same conditions.

The culture filtrates were collected as described in Example 21 and assayed for high pH endoglucanase activity as described above. The results are shown in Table 12.

TABLE 11

Production of high pH endoglucanase in *T. reesei* strains M2C38, 984A and 998A in 14 liter fermentations

| Strain | Vector | promoter | secretion signal | HECU/mg |
|---|---|---|---|---|
| M2C38 | none | none | none | 0 |
| 984A | pChHE2-TV | cbh1 | cbh1 | 0.097 |
| 998A | pC/XhHE2-TV | cbh1 | xln2 | 0.195 |

The untransformed strain produced 0 IU of high pH endoglucanase activity per mg protein. The transformant 984A with the cbh1 promoter and secretion signal produced 0.097 IU/mg while transformant 998A with the cbh1 promoter and the xln2 secretion signal produced 0.195 IU/mg which is 2 times more high pH endoglucanase activity than the transformant with the cbh1 secretion signal

Example 32
Construction of *Trametes versicolor* laccase I expression vectors pCL1-TV and pC/XL1 -TV This example describes the construction of vectors expressing the mature *T. versicolor* laccase I coding region under the control of the *T. reesei* cbh1 promoter and secretion signal or the *T. reesei* cbh1 promoter and xln2 secretion signal.

A cDNA clone of theEcoR *T. versicolor* laccase I gene (lcc1) was obtained from Edgar Ong in the phagemid vector pBK-CMV (Ong, Pollock and Smith, 1997, "Cloning and sequence analysis of two laccase complementary DNAs from the ligninolytic basidiomycete *Trametes versicolor*", Gene 196: 113–119, herein referred to as Ong et al.). The mature laccase coding region lacking its native secretion signal was amplified with Pwo and primers designed to introduce a unique XbaI site directly upstream of bp 250 and a unique XhoI site directly downstream of the stop codon at bp 1750 of the published lcc1 sequence (Ong et al.). The amplified sequence was inserted as a blunt-ended fragment into the unique EcoRV site of pBR322 to generate the plasmid pBRLcc1 and the sequence of the lcc1 fragment verified. In order to make the lcc1 expression cassette plasmids pCL1 and pC/XL1, an unique XhoI site was inserted at the 5' end of the cbh2 transcriptional terminator in the cmc3 expression cassette vectors pChHE2 and pC/XhHE2 by digestion with KpnI and blunting with T4 DNA polymerase, followed by ligation of XhoI linkers (Cat. No. 1073, New England Biolabs) to generate the modified cmc3 expression cassette plasmids pChHE2-Xho and pC/XhHE2-Xho. The lcc1 gene was isolated as a 1.5 kb fragment by XbaI/XhoI digestion of pBRLcc1 and was used to replace the cmc3 gene in the expression cassette plasmids pChHE2-Xho and pC/XhHE2-Xho which had been digested with NheI/XhoI (NheI and XbaI have compatible overhangs). The resulting lcc1 expression cassette plasmids contain the lcc1 gene linked to the cbh1 (in pCLI) orxln2 (pC/XL1) secretion signal under the control of the cbh1 promoter. To make the final transformation vectors pCL1-TV (FIG. 9a) and pC/XL1-TV (FIG. 9b), the lcc1 expression cassettes were isolated by EcoRI digestion of pCL1 and pC/XL1 and inserted into the unique EcoRI site of the pyr4 selection cassette plasmid pNCBgl (Example 23, above). The orientation of the insert was chosen such that the entire genetic construct comprising the lcc1 expression cassette and the *N. crassa* pyr4 selection cassette could be isolated away from the pUC sequences by XbaI digest. Prior to transformation of *T. reesei* strain BTR213aux28, the transformation vectors pCL1-TV and pC/XL1-TV were digested with XbaI, the fragments separated by agarose gel electrophoresis and the larger band containing the lcc1 constructs purified.

Example 33
Production of *T. versicolor* laccase I by native and transformed *T. reesei* strains

*T. reesei* strain BTR213aux28 was transformed by particle bombardment (Example 20) with genetic constructs from the vectors pCL1-TV and pC/XL1-TV encoding the mature *T. versicolor* laccase I enzyme linked to the cbh1 or xln2 secretion signal under the control of the cbh1 promoter. Secondary selection of pyr4+transformants was performed by spotting of individual colonies on minimal medium (Example 19) with 10% solka floc to induce the cbh1 promoter, 1.0 MM $CuSO_4$, 1.0 mM 2, 2'-azinobis-(3-ethylbenzthiazoline-6-sulfonic acid) (ABTS). Laccase-producing transformants are identified by the formation of a dark-green halo indicative of a one electron oxidation of the ABTS substrate.

The native strain BTR213 and the resulting transformed strains were cultured using the procedures of Example 21 with 10 g/l solka floc and 5 g/l glucose as carbon source.

Measurement of the Laccase Activity of an Enzyme Sample

Laccase activity is determined by oxidation of ABTS at 30° C. The assay mixture contains 0.5 mM ABTS, 0.1 M sodium acetate pH 5.0 and a suitable amount of enzyme. Oxidation of ABTS is followed by measuring the absorbance increase at 420 nm ($\epsilon_{420}=3.6\times10^4$ $M^{-1}*cm^{-1}$). One unit of laccase activity is the amount of enzyme required to oxidize one micromole of ABTS per minute.

The culture filtrates were collected as described in Example 21 and assayed for laccase activity as described above. The results indicated that increased levels of laccase were produced with transformants comprising the xylanase secretion signal (pC/XL1-TV), when compared to the untransformed host (BTR213), or when compared with *T. reesei* transformed with a vector comprising the cbh1 regulatory region and secretory signal.

Examples 34–38 describe the expression of a modified thermophilic *Trichodermna* xylanase in *Humicola insolens* using the *Trichoderma reesei* cbh1 promoter and xln2 secretion signal

Example 34
Construction of the Thermophilic *T. reesei* xln2 Expression Vector pC/XHTX4

The *T. reesei* xln2 gene, including the promoter and terminator regions, was cloned as described in Example 4, above. A 2.6 kb fragment encoding the xln2 promoter, secretion signal sequence and the first 8 amino acids of the secreted protein was amplified by the polymerase chain reaction from the xln2 subclone pXYN2K-2 Example 4) using Pwo polymerase (Boehringer) with proof-reading activity using an xln2-specific primer to introduce a unique PinAI site at bp 118–123 of the published xln2 sequence (Saarelainen et al.) and the pUC reverse primer (Cat. No. 18432-013, Gibco/BRL). The resulting blunt-ended fragment was inserted into the SmaI site of pUC119 to generate the plasmid pUC/xynssP. The amplified sequences were then isolated from pUC/xynssP as an EcoRI/BamHI fragment and inserted between the EcoRI and BamHI sites of pBR322L (Example 5) to generate pBR322LXP. A ~1.3 kp HindIII fragment comprising bp −1400 (approx.) to −121 of the xln2 promoter in pBR322LXP was replaced by a 1.2 kb HindIII fragment comprising bp −1399 to −204 of the *T. reesei* cbh1 promoter (GenBank Accession number D86235). The EcoRI site at the 5' end of the chimeric cbh1/xln2 regulatory region was then destroyed by blunting with Klenow and the addition of SpeI linkers. The coding region of xln2 was amplified from pXYN2K-2 using primers to introduce an PinAI site upstream of bp +99 and a KpnI site downstream of bp +780 of the published xln2 sequence (Saarelainen et al.) and inserted as a blunt fragment into the SmaI site of pUC119 to generate pTrxIIm-Pin. A modified xln2 synthetic gene was obtained from W. Sung (containing the gene NITX11 described in U.S. Pat. Nos. 5,759,840 and 5,866,408) and a 75 bp PinAI/ApaI fragment encoding amino acids 7–33 of the secreted xylanase II but with the mutations N10H, V27M, M29L was isolated and was used to replace the same region in pTrxIIm-Pin to make pHTX4-Pin. Using sites from the pUC119 polylinker in pHTX4-Pin, the modified xln2 gene was isolated as a 0.6 kb SphI/KpnI fragment and inserted between the SphI and KpnI sites upstream of the cbh2 terminator in pCB219N (Example 5). The resulting plasmid was then digested with PinAI and NotI to isolate a 2.4 kb fragment comprising sequences encoding amino acids 9–190 of the modified xylanase II enzyme (0.5 kb) and the cbh2 terminator (1.9 kb). This fragment was inserted downstream of the xln2 sequences in pBR322LXP, which had been digested with PinAI and NotI to make the expression cassette plasmid pC/XHTX4. The final transformation vector, pC/XHTX4-TV was prepared by isolating the expression cassette from pC/XHTX4 by digestion with NotI, blunting with Klenow followed by digestion with SpeI. This fragment was inserted upstream of the hph selection cassette in the plasmid pHPT136X (Example 6) which had been digested with XhoI, blunted with Klenow, then digested with XbaI (XbaI and SpeI have compatible overhangs). The final transformation vector pC/XHTX4-TV was linearized by NotI digestion prior to transformation of *Humicola insolens* strain ATCC22082 by particle bombardment as described in Example 35.

Example 35
Transformation of *H. insolens* ATCC strain 22082 with pHTX4-TV via microprojectile bombardment The Biolistic PDS-1000/He system (BioRad; E.I. DuPont de Nemours and Company) was used to transform spores of *H. insolens* strain ATCC22082 and all procedures were performed as recommended by the manufacturer. M-10 tungsten particles (median diameter of 0.7 um) were used as microcarriers. The following parameters were used in the optimization of the transformation: a rupture pressure of 1100 psi, a helium pressure of 29 mm Hg, a gap distance of 0.95 cm, a macrocarrier travel distance of 16 mm, and a target distance of 9 cm. Plates were prepared with $1\times10^6$ spores on Emerson YPSS agar (Difco). Bombarded plates were incubated at 37° C. Four hours post-bombardment, spores were subjected to primary selection by the overlaying of selective YPSS agar supplemented with 240 units/ml of HygB. The bombardment plates were incubated at 37° C. Transformants could be observed after 5–6 days growth. Individual colonies were subjected to secondary selection by isolation with a sterile toothpick and streaking onto individual YPSS agar plates containing 120 units/ml HygB. These secondary selection plates were further incubated for 5–6 days at 37° C.

Example 36
Production of a Modified Thermophilic *T. reesei* Xylanase in Liquid *H. insolens* Cultures This Example describes the methods used to express a modified thermophilic *T. reesei* xylanase enzyme from a *Humicola* strain.

Individual colonies of *H. insolens* were transferred to YPSS agar plates for the propagation of each culture. Sporulation is necessary for the uniform inoculation of shake flasks which are used in testing the ability of the culture to produce the β-glucosidase and cellulase. The culture media is composed of the following:

| Component | g/L |
|---|---|
| $(NH_4)_2SO_4$ | 6.35 |
| $KH_2PO_4$ | 4.00 |
| $MgSO_4$-$7H_2O$ | 2.02 |
| $CaCl_2$-$2H_2O$ | 0.53 |
| CSL | 6.25 |
| $CaCO_3$ | 10.00 |
| Trace elements* | 5–200 |
| Carbon sources** | 1 ml/L |

*Trace elements solution contains 5 g/l $FeSO_4$*$7H_2O$; 1.6 g/l $MnSO_4$*$H_2O$; 1.4 g/l $ZnSO_4$*$7H_2O$.
**glucose, Solka floc. The carbon source can be sterilized separately as an aqueous solution at pH 2 to 7 and added to the remaining media initially or through the course of the fermentation.

The liquid volume per 1-liter flask is 150 ml, the initial pH is 5.5 and each flask was sterilized by steam autoclave for 30 minutes at 121° C. prior to inoculation.

For both native and transformed cells, spores were isolated from the YPSS agar plates as previously described (Example 9) and $1-2 \times 10^6$ spores were used to inoculate each flask. The flasks were shaken at 200 rpm at a temperature of 37° C. for a period of 3 days. The filtrate containing the secreted protein was collected by filtration through GF/A glass microfibre filters (Whatman). The protein concentration was determined using the Bio-Rad Protein Assay (Cat. No. 500-0001).

Example 37
Determination of Thermophilic Xylanase Activity

The xylanase activity of the culture filtrates was measured at both 50° C. and 65° C. using a solid azo-xylan substrate (Megazyme) with some modifications of the manufacturer's protocol as described here. The substrate is prepared as follows: 1 gm of azo-xylan was added to 35 ml of water preheated to 80° C. and stirred for 60 min; 12.5 ml of 2.0 M acetate, pH 4.5 was then added and the volume adjusted to 50 ml; the final pH of the substrate was 4.4–4.7. For the 50° C. assay, the culture filtrate was diluted to several concentrations in 0.5 M acetate buffer, pH 4.5. For the 65° C. assay, the culture filtrate was diluted to several concentrations in 50 mM acetate buffer, pH 4.8. A convenient range of dilutions is 1–5 times the estimated activity of the sample. For example, a 1000 unit/ml sample should be diluted 1: 1000 to 1:5000. The diluted samples (0.2 ml each) and the substrate were preheated separately to 50° C. or 65° C. for 5 minutes, then a 0.25 ml aliquot of the azo-xylan substrate was added to each tube with enzyme. The test tubes were incubated for 10 minutes at 50° C. or 65° C. The reaction was terminated by the addition of 1 ml of 95% ethanol to each tube and vortexlng. Unreacted azo-xylan was removed by centrifugation (6 minutes at 2000×g, room temperature). The amount of azo dye released from the azo-xylan substrate by the xylanase was determined by measuring the absorbances of the supernatants at 590 nm, taking into account the small release of the dye from the substrate in the absence of enzyme. The activity of the culture is then calculated by comparing the ml of the culture filtrate required to give an absorbance of 0.5 at 590 nm compared the ml of a control xylanase enzyme solution of known activity required to give the same absorbance under the same conditions.

Example 38
Production of a Modified Thermophilic *T. reesei* Xylanase by *H. insolens* Strain 22082 and 22082-5A The vector pC/XHTX4-TV, in which a modified thermophilic *T. reesei* xylanase II is expressed from the cbh1 promoter and xln2 secretion signal, was introduced into *H. insolens* strain 22082 by particle bombardment as described in Example 35. The untransformed strain 22082 and the transformed strain from this host, 22082-5A were cultured using the procedures of Example 36 with 10 g/l Solka floc and 5 g/l glucose as carbon sources. The results are shown in Table 14.

TABLE 14

Production of a modified thermophilic *T. reesei* xylanase in *H. insolens* strains 22082 and 22082-5A in 150 ml flask cultures

| Strain | HTX4 promoter | HTX4 secretion signal | 50° C. XU/mg | 65° C. XU/mg |
|---|---|---|---|---|
| 22082 | none | none | 15.9 | 10.55 |
| 22082-5A | *T. reesei* cbh1 | *T. reesei* xln2 | 29.8 | 24.99 |

The untransformed strain produced 15.9 IU of 50° C. xylanase activity and 10.55 IU of 65° C. xylanase activity per mg protein. The transformant 22082-5A produced 29.8 IU of 50° C. xylanase activity and 24.99 IU of 65° C. xylanase activity per mg protein. This represents a 2.4-fold improvement in 65° C. xylanase activity over the untransformed strain.

This result indicates that the *T. reesei* cbh1 promoter and xln2 secretion signal are effective for the expression of a gene of interest, and the secretion of a protein of interest in a heterologous host.

All citations are herein incorporated by reference.

While the present invention has been described with respect to what is at present considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent formulations and functions.

We claim:

1. A nucleotide sequence comprising, a regulatory region selected from the group consisting of cbh1, cbh2, eg1, eg2, eg3, eg5, xln1, and xln2, in operative association with a xylanase secretion sequence and a gene of interest encoding a protein selected from the group consisting of a mannanase, a laccase, an endoglucanase, and a cellobiohydrolase.

2. The nucleotide sequence of claim 1 further comprising a terminator sequence.

3. The nucleotide sequence of claim 1 further comprising a selectable marker.

4. The nucleotide sequence of claim 1 further comprising an intervening sequence.

5. A vector comprising the nucleotide sequence of claim 1.

6. A transformed filamentous fungus comprising the vector of claim 5.

7. A transformed filamentous fungus comprising the nucleotide sequence of claim 1.

8. The transformed filamentous fungus of claim 7, wherein the filamentous fungus is selected from the group consisting of *Trichoderma, Humicola, Fusarium, Aspergillus, Mycogone, Verticillium, Colletotrichum, Neurospora, Botrytis, Pleurotus, Penicillium, Cephalosporium, Myrothecium, Papulospora, Achlya, Podospora, Endothia, Mucor, Cochilobbolus, Tolypocladium, Pyricularia, Penicillium, Myceliophthora, Irpex, Stachybotrys, Scorpulariopsis, Chaetomium, Gliocladium, Cephalosporin* and *Acremonium*.

9. The transformed filamentous fungus of claim 8, wherein the filamentous fungus is *Trichoderma*.

10. The transformed filamentous fungus of claim 8, wherein the filamentous fungus is *Humicola*.

11. A method of producing a protein of interest within a filamentous fungus comprising the steps of:
   i) transforming the filamentous fungus with a nucleotide sequence comprising, a regulatory region selected from the group consisting of cbh1, cbh2, eg1, eg2, eg3, eg5, xln1, and xln2, in operative association with a xylanase secretion sequence and a gene of interest selected from the group consisting of mannanases, laccases, endoglucanases, and cellobiohydrolases;
   ii) growing the filamentous fungus, and
   iii) causing the fungus to produce the protein of interest.

12. A method of producing a protein of interest within a filamentous fungus comprising the steps of:
   i) transforming the filamentous fungus with the nucleic acid sequence of claim 6;
   ii) growing the filamentous fungus; and
   iii) causing the fungus to produce the protein of interest.

13. The method of claim 12, wherein, in the step of transforming, the xylanase secretion sequence is heterologous with respect to the filamentous fungus.

14. The method of claim 12, wherein, in the step of transforming, the xylanase secretion sequence is homologous with respect to the filamentous fungus.

15. The method of claim 13, wherein, in the step of transforming, the xylanase secretion sequence is heterologous with respect to the filamentous fungus.

16. The method of claim 12, wherein, in the step of transforming, the xylanase secretion sequence is homologous with respect to the filamentous fungus.

17. The method of claim 12, further comprising purifying the protein of interest.

18. The method of claim 12, further comprising purifying the protein of interest.

19. The method of claim 12, further comprising removing the amino acid sequence encoded by the intervening sequence from the protein of interest.

20. The nucleotide sequence of claim 1, wherein the protein is selected from the group consisting of β-glucosidase, endogluconase II, mannanase, and laccase I.

21. A vector comprising the isolated nucleotide sequence of claim 20.

22. A transformed filamentous fungus comprising the vector of claim 21.

23. A transformed filamentous fungus comprising the nucleotide sequence of claim 20.

24. A method of producing a protein of interest within a filamentous fungus comprising the steps of:
   i) transforming the filamentous fungus with the vector of claim 21;
   ii) growing the filamentous fungus; and
   iii) causing the fungus to produce the protein.

25. A method of producing a protein of interest within a filamentous fungus comprising the steps of:
   i) transforming the filamentous fungus with the vector of claim 20;
   ii) growing the filamentous fungus; and
   iii) causing the fungus to produce the protein.

26. The nucleotide sequence of claim 1, wherein said xylanase secretion signal is a family 11 xylanase secretion signal.

27. The nucleotide sequence of claim 1, wherein said xylanase secretion signal is a xylanase II secretion signal.

* * * * *

SEQUENCE LISTING (1) GENERAL INFORMATION:

(iii) NUMBER OF SEQUENCES: 4

-continued

```
(2) INFORMATION FOR SEQ ID NO: 1:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Trichoderma reesei (ix) FEATURE:
        (A) NAME/KEY: sig_peptide
        (B) LOCATION: 1..51
        (D) OTHER INFORMATION: /function= "cbh1 secretion signal"

(ix) FEATURE:
        (A) NAME/KEY: mat_peptide
        (B) LOCATION: 61..72
        (D) OTHER INFORMATION: /function= "mature
            beta-glucosidase"

(ix) FEATURE:
        (A) NAME/KEY: CDS
        (B) LOCATION: 1..72

(xi) SEQUENCE DESCRIPTION: SEQ ID NO: 1:

ATG TAT CGG AAG TTG GCC GTC ATC TCG GCC TTC TTG GCC ACA GCT CGT      48
Met Tyr Arg Lys Leu Ala Val Ile Ser Ala Phe Leu Ala Thr Ala Arg
-20             -15                 -10                 -5

GCT CAG TCG GCA GTT GTA CCT CCT                                      72
Ala Gln Ser Ala Val Val Pro Pro
                1

(2) INFORMATION FOR SEQ ID NO: 2:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO: 2:

Met Tyr Arg Lys Leu Ala Val Ile Ser Ala Phe Leu Ala Thr Ala Arg
-20             -15                 -10                 -5

Ala Gln Ser Ala Val Val Pro Pro
                1

(2) INFORMATION FOR SEQ ID NO: 3:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Trichoderma reesei (ix) FEATURE:
        (A) NAME/KEY: sig_peptide
        (B) LOCATION: 1..99
```

-continued

```
        (D) OTHER INFORMATION: /function= "xln 2 signal peptide"

(ix) FEATURE:
        (A) NAME/KEY: mat_peptide
        (B) LOCATION: 109..120
        (D) OTHER INFORMATION: /function= "mature
            beta-glucosidase"

(ix) FEATURE:
        (A) NAME/KEY: CDS
        (B) LOCATION: 1..120

(xi) SEQUENCE DESCRIPTION: SEQ ID NO: 3:

ATG GTC TCC TTC ACC TCC CTC CTC GCC GGC GTC GCC GCC ATC TCG GGC        48
Met Val Ser Phe Thr Ser Leu Leu Ala Gly Val Ala Ala Ile Ser Gly
-36 -35              -30                 -25

GTC TTG GCC GCT CCC GCC GCC GAG GTC GAA TCC GTG GCT GTG GAG AAG        96
Val Leu Ala Ala Pro Ala Ala Glu Val Glu Ser Val Ala Val Glu Lys
-20              -15                 -10                 -5

CGC CAG GCT AGA GTT GTA CCT CCT                                       120
Arg Gln Ala Arg Val Val Pro Pro
                1

(2) INFORMATION FOR SEQ ID NO: 4:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO: 4:

Met Val Ser Phe Thr Ser Leu Leu Ala Gly Val Ala Ala Ile Ser Gly
-36 -35              -30                 -25

Val Leu Ala Ala Pro Ala Ala Glu Val Glu Ser Val Ala Val Glu Lys
-20              -15                 -10                 -5

Arg Gln Ala Arg Val Val Pro Pro
                1
```